United States Patent
Zhou

(10) Patent No.: US 12,378,697 B2
(45) Date of Patent: Aug. 5, 2025

(54) METHOD FOR PREPARING PHAGE LIBRARY

(71) Applicant: DDBIO. CO, LTD., (SHANG HAI), Shanghai (CN)

(72) Inventor: Chen Zhou, Shanghai (CN)

(73) Assignee: DDBIO. CO, LTD., (SHANG HAI), Shanghai (CN)

(*) Notice: Subject to any disclaimer, the term of this patent is extended or adjusted under 35 U.S.C. 154(b) by 806 days.

(21) Appl. No.: 17/605,409

(22) PCT Filed: Apr. 20, 2020

(86) PCT No.: PCT/CN2020/085706
§ 371 (c)(1),
(2) Date: Oct. 21, 2021

(87) PCT Pub. No.: WO2020/216191
PCT Pub. Date: Oct. 29, 2020

(65) Prior Publication Data
US 2022/0228138 A1 Jul. 21, 2022

(30) Foreign Application Priority Data
Apr. 22, 2019 (CN) .......................... 201910327739.6

(51) Int. Cl.
*C40B 50/06* (2006.01)
*C07K 16/00* (2006.01)

(52) U.S. Cl.
CPC ............ *C40B 50/06* (2013.01); *C07K 16/005* (2013.01); *C07K 2317/55* (2013.01)

(58) Field of Classification Search
None
See application file for complete search history.

(56) References Cited

U.S. PATENT DOCUMENTS

| | | |
|---|---|---|
| 5,565,332 A | 10/1996 | Hoogenboom et al. |
| 6,261,558 B1 | 7/2001 | Barbas et al. |

(Continued)

FOREIGN PATENT DOCUMENTS

| | | |
|---|---|---|
| CN | 101210241 A | 7/2008 |
| CN | 101619323 A | 1/2010 |

(Continued)

OTHER PUBLICATIONS

Zhou et al. (2011) Acta Biochimica Biophysica Sinica vol. 43 pp. 232 to 238 (Year: 2011).*

(Continued)

*Primary Examiner* — Christian C Boesen
(74) *Attorney, Agent, or Firm* — Merchant & Gould P.C.; Daniel J. Pereira

(57) ABSTRACT

Provided is method for producing a phage library displaying antibodies or antibody fragments, comprising providing a first polynucleotide containing LC, a second polynucleotide containing connexon, and a third polynucleotide containing HC, respectively introducing the first, second and third polynucleotides to first, second and third bacteria to obtain a light chain component bacterial library, a connexon component bacterial library, and a heavy chain component bacterial library, obtaining a light chain component plasmid, a connexon component plasmid, and a heavy chain component plasmid from the libraries, obtaining the released LC, released connexon and released HC from the plasmids, connecting the released display vector segments to form a connection product for display, introducing a third bacterium to obtain a display bacterial library, and using the display bacterial library to prepare the phage library for displaying the antibodies or antibody fragments. Also provided is a phage library produced according to the method.

22 Claims, 4 Drawing Sheets

Specification includes a Sequence Listing.

(56) References Cited

U.S. PATENT DOCUMENTS

| | | |
|---|---|---|
| 2010/0137156 A1 | 6/2010 | Leung et al. |
| 2019/0085323 A1 | 3/2019 | Yang et al. |

FOREIGN PATENT DOCUMENTS

| | | |
|---|---|---|
| CN | 101720368 A | 6/2010 |
| CN | 102732974 A | 10/2012 |
| RU | 2 311 927 C2 | 12/2007 |
| RU | 2 402 777 C2 | 10/2010 |
| WO | WO 03/029456 A1 | 4/2003 |
| WO | WO 2018/002952 A2 | 1/2018 |

OTHER PUBLICATIONS

International Search Report issued on Jul. 27, 2020 in PCT/CN2020/085706 filed on Apr. 20, 2020, 3 pages.

Cen, X. et al., "Construction of a large phage display antibody library by in vitro package and in vivo recombination," Appl. Microbiol. Biotechnol., vol. 71, 2006, pp. 767-772.

Nishizaki, T. et al., "Metabolic Engineering of Carotenoid Biosynthesis in *Escherichia coli* by Ordered Gene Assembly in *Bacillus subtilis*," Applied and Environmental Microbiology, vol. 73, No. 4, 2007, pp. 1355-1361.

Tsuge, K. et al., "One step assembly of multiple DNA fragments with a designed order and orientation in *Bacillus subtilis* plasmid," Nucleic Acids Research, vol. 31, No. 21, e133, 2003, pp. 1-8.

Lu, C. et al., "Comparison of Multiple Gene Assembly Methods for Metabolic Engineering," Applied Biochemistry and Biotechnology, vol. 136-140, 2007, pp. 703-710.

Russian Office Action issued Jan. 15, 2024 in Russian Patent Application No. 2021133710/10(071211) (with English translation), 21 pages.

Japanese Office Action issued Feb. 27, 2024 in Japanese Patent Application No. 2021-562852, 5 pages.

Crameri, A. et al., "Construction and evolution of antibody-phage libraries by DNA shuffling," Nature Medicine, vol. 2, No. 1, Jan. 1996, 3 pages.

Nelson, R. et al., "A universal phage display system for the seamless construction of Fab libraries," Journal of Immunological Methods, vol. 450, 2017, pp. 41-49.

Extended European Search Report issued Dec. 16, 2022 in European Patent Application No. 20794500.7, 11 pages.

European Office Action issued Jan. 11, 2023 in European Patent Application No. 20794500.7, 1 page.

Schwimmer et al., "Discovery of Diverse and Functional antibodies from large human repertoire antibody libraries", Journal of Immunological Methods, vol. 391, No. 1, Feb. 27, 2013, pp. 60-71, XP028545144.

* cited by examiner

SEQUENCE LISTING

<160> NUMBER OF SEQ ID NOS: 100

<210> SEQ ID NO 1
<211> LENGTH: 13
<212> TYPE: DNA
<213> ORGANISM: Artificial Sequence
<220> FEATURE:
<223> OTHER INFORMATION: R1/R8

<400> SEQUENCE: 1
ggcccaggcg gcc                                                        13

<210> SEQ ID NO 2
<211> LENGTH: 13
<212> TYPE: DNA
<213> ORGANISM: Artificial Sequence
<220> FEATURE:
<223> OTHER INFORMATION: R2/R3

<400> SEQUENCE: 2
ggccacatag gcc                                                        13

<210> SEQ ID NO 3
<211> LENGTH: 13
<212> TYPE: DNA
<213> ORGANISM: Artificial Sequence
<220> FEATURE:
<223> OTHER INFORMATION: R4/R5

<400> SEQUENCE: 3
ggcccaaccg gcc                                                        13

<210> SEQ ID NO 4
<211> LENGTH: 12
<212> TYPE: DNA
<213> ORGANISM: Artificial Sequence
<220> FEATURE:
<223> OTHER INFORMATION: R6/R7

<400> SEQUENCE: 4
cgtctcctca gc                                                         12

```
<210> SEQ ID NO 5
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 5
tcgctaccgt ggcccaggcg gccgacatcc agatgaccca gtctcc          46

<210> SEQ ID NO 6
<211> LENGTH: 48
<212> TYPE: DNA
<213> ORGANISM: Artificial Sequence
<220> FEATURE:
<223> OTHER INFORMATION: Forward primer of light chain KLC

<400> SEQUENCE: 6
tcgctaccgt ggcccaggcg gccgatattg tgatgaccca gactccac        48

<210> SEQ ID NO 7
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 7
tcgctaccgt ggcccaggcg gccgccatcc agttgaccca gtctcc          46

<210> SEQ ID NO 8
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 8
tcgctaccgt ggcccaggcg gccgccatcc ggatgaccca gtctcc          46

<210> SEQ ID NO 9
<211> LENGTH: 48
<212> TYPE: DNA
<213> ORGANISM: Artificial Sequence
<220> FEATURE:
<223> OTHER INFORMATION: Forward primer of light chain KLC

<400> SEQUENCE: 9
tcgctaccgt ggcccaggcg gccgatgttg tgatgactca gtctccac        48

<210> SEQ ID NO 10
<211> LENGTH: 48
<212> TYPE: DNA
<213> ORGANISM: Artificial Sequence
<220> FEATURE:
<223> OTHER INFORMATION: Forward primer of light chain KLC

<400> SEQUENCE: 10
tcgctaccgt ggcccaggcg gccgatattg tgatgactca gtctccac        48

<210> SEQ ID NO 11
<211> LENGTH: 48
<212> TYPE: DNA
<213> ORGANISM: Artificial Sequence
<220> FEATURE:
<223> OTHER INFORMATION: Forward primer of light chain KLC
```

<400> SEQUENCE: 11
tcgctaccgt ggcccaggcg gccgaaattg tgttgacgca gtctccag        48

<210> SEQ ID NO 12
<211> LENGTH: 48
<212> TYPE: DNA
<213> ORGANISM: Artificial Sequence
<220> FEATURE:
<223> OTHER INFORMATION: Forward primer of light chain KLC

<400> SEQUENCE: 12
tcgctaccgt ggcccaggcg gccgaaatag tgatgacgca gtctccag        48

<210> SEQ ID NO 13
<211> LENGTH: 48
<212> TYPE: DNA
<213> ORGANISM: Artificial Sequence
<220> FEATURE:
<223> OTHER INFORMATION: Forward primer of light chain KLC

<400> SEQUENCE: 13
tcgctaccgt ggcccaggcg gccgaaattg tgttgacaca gtctccag        48

<210> SEQ ID NO 14
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 14
tcgctaccgt ggcccaggcg gccgaaattg tgctgactca gtctcc        46

<210> SEQ ID NO 15
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 15
tcgctaccgt ggcccaggcg gccaacatcc agatgaccca gtctcc        46

<210> SEQ ID NO 16
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 16
tcgctaccgt ggcccaggcg gccgacatcc agttgaccca gtctcc        46

<210> SEQ ID NO 17
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 17
tcgctaccgt ggcccaggcg gccgtcatct ggatgaccca gtctcc        46

<210> SEQ ID NO 18
<211> LENGTH: 46

```
<212> TYPE: DNA
<213> ORGANISM: Artificial Sequence
<220> FEATURE:
<223> OTHER INFORMATION: Forward primer of light chain KLC

<400> SEQUENCE: 18
tcgctaccgt ggcccaggcg gccgccatcc agatgaccca gtctcc           46

<210> SEQ ID NO 19
<211> LENGTH: 49
<212> TYPE: DNA
<213> ORGANISM: Artificial Sequence
<220> FEATURE:
<223> OTHER INFORMATION: Forward primer of light chain KLC

<400> SEQUENCE: 19
tcgctaccgt ggcccaggcg gccgaaattg taatgacaca gtctccagc         49

<210> SEQ ID NO 20
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 20
tcgctaccgt ggcccaggcg gccgacatcg tgatgaccca gtctcc           46

<210> SEQ ID NO 21
<211> LENGTH: 46
<212> TYPE: DNA
<213> ORGANISM: Artificial Sequence
<220> FEATURE:
<223> OTHER INFORMATION: Forward primer of light chain KLC

<400> SEQUENCE: 21
tcgctaccgt ggcccaggcg gccgaaacga cactcacgca gtctcc           46

<210> SEQ ID NO 22
<211> LENGTH: 48
<212> TYPE: DNA
<213> ORGANISM: Artificial Sequence
<220> FEATURE:
<223> OTHER INFORMATION: Forward primer of light chain KLC

<400> SEQUENCE: 22
tcgctaccgt ggcccaggcg gccgatgttg tgatgacaca gtctccag         48

<210> SEQ ID NO 23
<211> LENGTH: 51
<212> TYPE: DNA
<213> ORGANISM: Artificial Sequence
<220> FEATURE:
<223> OTHER INFORMATION: Reverse primer of light chain KLC

<400> SEQUENCE: 23
taaattcctc ggcctatgtg gcctattaac actctcccct gttgaagctc t      51

<210> SEQ ID NO 24
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 24
```

```
tcgctaccgt ggcccaggcg gcccagtctg tgctgactca gccacc                    46

<210> SEQ ID NO 25
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 25
tcgctaccgt ggcccaggcg gcccagtctg ccctgactca gcctc                     45

<210> SEQ ID NO 26
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 26
tcgctaccgt ggcccaggcg gcccagtctg ccctgactca gcctg                     45

<210> SEQ ID NO 27
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 27
tcgctaccgt ggcccaggcg gcctcctatg agctgacaca gccacc                    46

<210> SEQ ID NO 28
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 28
tcgctaccgt ggcccaggcg gcctcctatg agctgacaca gccatc                    46

<210> SEQ ID NO 29
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 29
tcgctaccgt ggcccaggcg gcctcctatg agctgactca gccacc                    46

<210> SEQ ID NO 30
<211> LENGTH: 47
<212> TYPE: DNA
<213> ORGANISM: Artificial Sequence
<220> FEATURE:
<223> OTHER INFORMATION: Forward primer of light chain LLC

<400> SEQUENCE: 30
tcgctaccgt ggcccaggcg gcctcctatg agctgactca gccactc                   47

<210> SEQ ID NO 31
<211> LENGTH: 46
<212> TYPE: DNA
<213> ORGANISM: Artificial Sequence
```

<220> FEATURE:
<223> OTHER INFORMATION: Forward primer of light chain LLC

<400> SEQUENCE: 31
tcgctaccgt ggcccaggcg gcccagtctg tgctgacgca gccgcc        46

<210> SEQ ID NO 32
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 32
tcgctaccgt ggcccaggcg gcccagtctg tgttgacgca gccgc         45

<210> SEQ ID NO 33
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 33
tcgctaccgt ggcccaggcg gcctcttctg agctgactca ggaccc        46

<210> SEQ ID NO 34
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 34
tcgctaccgt ggcccaggcg gcctcctatg tgctgactca gccacc        46

<210> SEQ ID NO 35
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 35
tcgctaccgt ggcccaggcg gcctcctatg agctgacaca gctacc        46

<210> SEQ ID NO 36
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 36
tcgctaccgt ggcccaggcg gcctcctatg agctgatgca gccacc        46

<210> SEQ ID NO 37
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 37
tcgctaccgt ggcccaggcg gccctgcctg tgctgactca gcccc         45

<210> SEQ ID NO 38
<211> LENGTH: 47
<212> TYPE: DNA
<213> ORGANISM: Artificial Sequence
<220> FEATURE:
<223> OTHER INFORMATION: Forward primer of light chain LLC

<400> SEQUENCE: 38
tcgctaccgt ggcccaggcg gcccagcctg tgctgactca atcatcc        47

<210> SEQ ID NO 39
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 39
tcgctaccgt ggcccaggcg gcccagcttg tgctgactca atcgcc         46

<210> SEQ ID NO 40
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 40
tcgctaccgt ggcccaggcg gcccagcctg tgctgactca gccacc         46

<210> SEQ ID NO 41
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 41
tcgctaccgt ggcccaggcg gcccaggctg tgctgactca gccgg          45

<210> SEQ ID NO 42
<211> LENGTH: 46
<212> TYPE: PRT
<213> ORGANISM: Artificial Sequence
<220> FEATURE:
<223> OTHER INFORMATION: Forward primer of light chain LLC

<400> SEQUENCE: 42

Thr Cys Gly Cys Thr Ala Cys Cys Gly Thr Gly Gly Cys Cys Cys Ala
1               5                   10                  15
Gly Gly Cys Gly Gly Cys Cys Cys Ala Gly Cys Cys Thr Gly Thr Gly
                20                  25                  30
Cys Thr Gly Ala Cys Thr Cys Ala Gly Cys Cys Ala Thr Cys
            35                  40                  45

<210> SEQ ID NO 43
<211> LENGTH: 47
<212> TYPE: DNA
<213> ORGANISM: Artificial Sequence
<220> FEATURE:
<223> OTHER INFORMATION: Forward primer of light chain LLC

<400> SEQUENCE: 43
tcgctaccgt ggcccaggcg gccaatttta tgctgactca gccccac        47

<210> SEQ ID NO 44
<211> LENGTH: 46
<212> TYPE: DNA
<213> ORGANISM: Artificial Sequence
<220> FEATURE:
<223> OTHER INFORMATION: Forward primer of light chain LLC

<400> SEQUENCE: 44
tcgctaccgt ggcccaggcg gcccagactg tggtgactca ggagcc         46

<210> SEQ ID NO 45
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 45
tcgctaccgt ggcccaggcg gcccaggctg tggtgactca ggagc          45

<210> SEQ ID NO 46
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 46
tcgctaccgt ggcccaggcg gcccagactg tggtgaccca ggagc          45

<210> SEQ ID NO 47
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 47
tcgctaccgt ggcccaggcg gcccagcctg tgctgactca gccac          45

<210> SEQ ID NO 48
<211> LENGTH: 45
<212> TYPE: DNA
<213> ORGANISM: Artificial Sequence
<220> FEATURE:
<223> OTHER INFORMATION: Forward primer of light chain LLC

<400> SEQUENCE: 48
tcgctaccgt ggcccaggcg gcccaggcag ggctgactca gccac          45

<210> SEQ ID NO 49
<211> LENGTH: 51
<212> TYPE: DNA
<213> ORGANISM: Artificial Sequence
<220> FEATURE:
<223> OTHER INFORMATION: Reverse primer of light chain LLC

<400> SEQUENCE: 49
taaattcctc ggcctatgtg gcctattatg aacattctgt aggggccact g      51

<210> SEQ ID NO 50
<211> LENGTH: 51
<212> TYPE: DNA
<213> ORGANISM: Artificial Sequence
<220> FEATURE:
<223> OTHER INFORMATION: Forward primer of VH

```
<400> SEQUENCE: 50
tattacttgc ggcccaaccg gccatggccg aggtgcagct ggtggagtct g          51

<210> SEQ ID NO 51
<211> LENGTH: 51
<212> TYPE: DNA
<213> ORGANISM: Artificial Sequence
<220> FEATURE:
<223> OTHER INFORMATION: Forward primer of VH

<400> SEQUENCE: 51
tattacttgc ggcccaaccg gccatggccc aggtgcagct gcaggagtcg g          51

<210> SEQ ID NO 52
<211> LENGTH: 51
<212> TYPE: DNA
<213> ORGANISM: Artificial Sequence
<220> FEATURE:
<223> OTHER INFORMATION: Forward primer of VH

<400> SEQUENCE: 52
tattacttgc ggcccaaccg gccatggccc aggtgcagct ggtgcagtct g          51

<210> SEQ ID NO 53
<211> LENGTH: 51
<212> TYPE: DNA
<213> ORGANISM: Artificial Sequence
<220> FEATURE:
<223> OTHER INFORMATION: Forward primer of VH

<400> SEQUENCE: 53
tattacttgc ggcccaaccg gccatggccc aggtgcagct ggtggagtct g          51

<210> SEQ ID NO 54
<211> LENGTH: 52
<212> TYPE: DNA
<213> ORGANISM: Artificial Sequence
<220> FEATURE:
<223> OTHER INFORMATION: Forward primer of VH

<400> SEQUENCE: 54
tattacttgc ggcccaaccg gccatggccc aggtcacctt gaaggagtct gg         52

<210> SEQ ID NO 55
<211> LENGTH: 52
<212> TYPE: DNA
<213> ORGANISM: Artificial Sequence
<220> FEATURE:
<223> OTHER INFORMATION: Forward primer of VH

<400> SEQUENCE: 55
tattacttgc ggcccaaccg gccatggccg aagtgcagct ggtggagtct gg         52

<210> SEQ ID NO 56
<211> LENGTH: 52
<212> TYPE: DNA
<213> ORGANISM: Artificial Sequence
<220> FEATURE:
<223> OTHER INFORMATION: Forward primer of VH

<400> SEQUENCE: 56
tattacttgc ggcccaaccg gccatggccc aggtccagct tgtgcagtct gg         52

<210> SEQ ID NO 57
```

```
<211> LENGTH: 52
<212> TYPE: DNA
<213> ORGANISM: Artificial Sequence
<220> FEATURE:
<223> OTHER INFORMATION: Forward primer of VH

<400> SEQUENCE: 57
tattacttgc ggcccaaccg gccatggccc aggttcagct ggtgcagtct gg          52

<210> SEQ ID NO 58
<211> LENGTH: 52
<212> TYPE: DNA
<213> ORGANISM: Artificial Sequence
<220> FEATURE:
<223> OTHER INFORMATION: Forward primer of VH

<400> SEQUENCE: 58
tattacttgc ggcccaaccg gccatggccc aggtccagct ggtacagtct gg          52

<210> SEQ ID NO 59
<211> LENGTH: 52
<212> TYPE: DNA
<213> ORGANISM: Artificial Sequence
<220> FEATURE:
<223> OTHER INFORMATION: Forward primer of VH

<400> SEQUENCE: 59
tattacttgc ggcccaaccg gccatggccc agatgcagct ggtgcagtct gg          52

<210> SEQ ID NO 60
<211> LENGTH: 52
<212> TYPE: DNA
<213> ORGANISM: Artificial Sequence
<220> FEATURE:
<223> OTHER INFORMATION: Forward primer of VH

<400> SEQUENCE: 60
tattacttgc ggcccaaccg gccatggccc aaatgcagct ggtgcagtct gg          52

<210> SEQ ID NO 61
<211> LENGTH: 52
<212> TYPE: DNA
<213> ORGANISM: Artificial Sequence
<220> FEATURE:
<223> OTHER INFORMATION: Forward primer of VH

<400> SEQUENCE: 61
tattacttgc ggcccaaccg gccatggccg aggtccagct ggtacagtct gg          52

<210> SEQ ID NO 62
<211> LENGTH: 52
<212> TYPE: DNA
<213> ORGANISM: Artificial Sequence
<220> FEATURE:
<223> OTHER INFORMATION: Forward primer of VH

<400> SEQUENCE: 62
tattacttgc ggcccaaccg gccatggccc agatcacctt gaaggagtct gg          52

<210> SEQ ID NO 63
<211> LENGTH: 52
<212> TYPE: DNA
<213> ORGANISM: Artificial Sequence
<220> FEATURE:
<223> OTHER INFORMATION: Forward primer of VH

<400> SEQUENCE: 63
```

-continued tattacttgc ggcccaaccg gccatggccg aggtgcagct gttggagtct gg    52

<210> SEQ ID NO 64
<211> LENGTH: 51
<212> TYPE: DNA
<213> ORGANISM: Artificial Sequence
<220> FEATURE:
<223> OTHER INFORMATION: Forward primer of VH

<400> SEQUENCE: 64
tattacttgc ggcccaaccg gccatggccg aggtgcagct ggtggagact g    51

<210> SEQ ID NO 65
<211> LENGTH: 52
<212> TYPE: DNA
<213> ORGANISM: Artificial Sequence
<220> FEATURE:
<223> OTHER INFORMATION: Forward primer of VH

<400> SEQUENCE: 65
tattacttgc ggcccaaccg gccatggccg aggtgcagct ggtggagtcc gg    52

<210> SEQ ID NO 66
<211> LENGTH: 52
<212> TYPE: DNA
<213> ORGANISM: Artificial Sequence
<220> FEATURE:
<223> OTHER INFORMATION: Forward primer of VH

<400> SEQUENCE: 66
tattacttgc ggcccaaccg gccatggccg aggtgcagct ggtggagtct cg    52

<210> SEQ ID NO 67
<211> LENGTH: 52
<212> TYPE: DNA
<213> ORGANISM: Artificial Sequence
<220> FEATURE:
<223> OTHER INFORMATION: Forward primer of VH

<400> SEQUENCE: 67
tattacttgc ggcccaaccg gccatggccc agctgcagct gcaggagtcc gg    52

<210> SEQ ID NO 68
<211> LENGTH: 52
<212> TYPE: DNA
<213> ORGANISM: Artificial Sequence
<220> FEATURE:
<223> OTHER INFORMATION: Forward primer of VH

<400> SEQUENCE: 68
tattacttgc ggcccaaccg gccatggccc aggtgcagct acagcagtgg gg    52

<210> SEQ ID NO 69
<211> LENGTH: 52
<212> TYPE: DNA
<213> ORGANISM: Artificial Sequence
<220> FEATURE:
<223> OTHER INFORMATION: Forward primer of VH

<400> SEQUENCE: 69
tattacttgc ggcccaaccg gccatggccc agctgcagct gcaggagtcg gg    52

<210> SEQ ID NO 70
<211> LENGTH: 52
<212> TYPE: DNA

```
<213> ORGANISM: Artificial Sequence
<220> FEATURE:
<223> OTHER INFORMATION: Forward primer of VH

<400> SEQUENCE: 70
tattacttgc ggcccaaccg gccatggccg aggtgcagct ggtgcagtct gg         52

<210> SEQ ID NO 71
<211> LENGTH: 52
<212> TYPE: DNA
<213> ORGANISM: Artificial Sequence
<220> FEATURE:
<223> OTHER INFORMATION: Forward primer of VH

<400> SEQUENCE: 71
tattacttgc ggcccaaccg gccatggccg aagtgcagct ggtgcagtct gg         52

<210> SEQ ID NO 72
<211> LENGTH: 52
<212> TYPE: DNA
<213> ORGANISM: Artificial Sequence
<220> FEATURE:
<223> OTHER INFORMATION: Forward primer of VH

<400> SEQUENCE: 72
tattacttgc ggcccaaccg gccatggccc aggtacagct gcagcagtca gg         52

<210> SEQ ID NO 73
<211> LENGTH: 52
<212> TYPE: DNA
<213> ORGANISM: Artificial Sequence
<220> FEATURE:
<223> OTHER INFORMATION: Forward primer of VH

<400> SEQUENCE: 73
tattacttgc ggcccaaccg gccatggccc aggtgcagct ggtgcaatct gg         52

<210> SEQ ID NO 74
<211> LENGTH: 42
<212> TYPE: DNA
<213> ORGANISM: Artificial Sequence
<220> FEATURE:
<223> OTHER INFORMATION: Reverse primer of VH

<400> SEQUENCE: 74
cttggtggag gctgaggaga cggtgaccag ggtgccctgg cc                    42

<210> SEQ ID NO 75
<211> LENGTH: 42
<212> TYPE: DNA
<213> ORGANISM: Artificial Sequence
<220> FEATURE:
<223> OTHER INFORMATION: Reverse primer of VH

<400> SEQUENCE: 75
cttggtggag gctgaggaga cggtgaccag ggtgccacgg cc                    42

<210> SEQ ID NO 76
<211> LENGTH: 42
<212> TYPE: DNA
<213> ORGANISM: Artificial Sequence
<220> FEATURE:
<223> OTHER INFORMATION: Reverse primer of VH

<400> SEQUENCE: 76
cttggtggag gctgaggaga cggtgaccat tgtcccttgg cc                    42
```

<210> SEQ ID NO 77
<211> LENGTH: 42
<212> TYPE: DNA
<213> ORGANISM: Artificial Sequence
<220> FEATURE:
<223> OTHER INFORMATION: Forward primer of VH

<400> SEQUENCE: 77
cttggtggag gctgaggaga cggtgaccag ggttccctgg cc                42

<210> SEQ ID NO 78
<211> LENGTH: 42
<212> TYPE: DNA
<213> ORGANISM: Artificial Sequence
<220> FEATURE:
<223> OTHER INFORMATION: Reverse primer of VH

<400> SEQUENCE: 78
cttggtggag gctgaggaga cggtgaccgt ggtcccttgg cc                42

<210> SEQ ID NO 79
<211> LENGTH: 22
<212> TYPE: DNA
<213> ORGANISM: Artificial Sequence
<220> FEATURE:
<223> OTHER INFORMATION: Forward primer of connexon

<400> SEQUENCE: 79
acagcttgtc tgtaagcgga tg                                      22

<210> SEQ ID NO 80
<211> LENGTH: 22
<212> TYPE: DNA
<213> ORGANISM: Artificial Sequence
<220> FEATURE:
<223> OTHER INFORMATION: Reverse primer of connexon

<400> SEQUENCE: 80
tgtggataac cgtattaccg cc                                      22

<210> SEQ ID NO 81
<211> LENGTH: 59
<212> TYPE: DNA
<213> ORGANISM: Artificial Sequence
<220> FEATURE:
<223> OTHER INFORMATION: Forward primer of R1-1kb-R2

<400> SEQUENCE: 81
ttagcgaatt ccagacatct aatggcccag gcggcctcag ctagcaccaa gggcccatc      59

<210> SEQ ID NO 82
<211> LENGTH: 59
<212> TYPE: DNA
<213> ORGANISM: Artificial Sequence
<220> FEATURE:
<223> OTHER INFORMATION: Reverse primer of  of R1-1kb-R2

<400> SEQUENCE: 82
cgggtgatca ccagtcttct attggcctat gtggccttat catttacccg gagacaggg      59

<210> SEQ ID NO 83
<211> LENGTH: 55
<212> TYPE: DNA
<213> ORGANISM: Artificial Sequence
<220> FEATURE:

<223> OTHER INFORMATION: Forward primer of R3-connexon-R4

<400> SEQUENCE: 83
taggccacat aggccgagga atttaaaatg aaatacctat tgcctacggc agccg        55

<210> SEQ ID NO 84
<211> LENGTH: 54
<212> TYPE: DNA
<213> ORGANISM: Artificial Sequence
<220> FEATURE:
<223> OTHER INFORMATION: Reverse primer of R3-connexon-R4

<400> SEQUENCE: 84
atggccggtt gggccgcaag taataacaat ccagcggctg ccgtaggcaa tagg         54

<210> SEQ ID NO 85
<211> LENGTH: 59
<212> TYPE: DNA
<213> ORGANISM: Artificial Sequence
<220> FEATURE:
<223> OTHER INFORMATION: Forward primer of R5-1kb-R6

<400> SEQUENCE: 85
ttagcgaatt ccagacatct aatggcccaa ccggcctcag ctagcaccaa gggcccatc    59

<210> SEQ ID NO 86
<211> LENGTH: 51
<212> TYPE: DNA
<213> ORGANISM: Artificial Sequence
<220> FEATURE:
<223> OTHER INFORMATION: Reverse primer of R5-1kb-R6

<400> SEQUENCE: 86
tgatcaccag tcttctattg gctgaggaga cgttatcatt tacccggaga c            51

<210> SEQ ID NO 87
<211> LENGTH: 987
<212> TYPE: DNA
<213> ORGANISM: Homo sapiens

<400> SEQUENCE: 87
tcagctagca ccaagggccc atcggtcttc cccctggcgc cctgctccag gagcacctcc    60
gagagcacag cggccctggg ctgcctggtc aaggactact cccccgaacc ggtgacggtg   120
tcgtggaact caggcgctct gaccagcggc gtgcacacct tcccagctgt cctacagtcc   180
tcaggactct actccctcag cagcgtggtg accgtgccct ccagcaactt cggcacccag   240
acctacacct gcaacgtaga tcacaagccc agcaacacca aggtggacaa gacagttgag   300
cgcaaatgtt gtgtcgagtg cccaccgtgc ccagcaccac ctgtggcagg accgtcagtc   360
ttcctcttcc ccccaaaacc caaggacacc ctcatgatct cccggacccc tgaggtcacg   420
tgcgtggtgg tggacgtgag ccacgaagac cccgaggtcc agttcaactg gtacgtggac   480
ggcgtggagg tgcataatgc caagacaaag ccacgggagg agcagttcaa cagcacgttc   540
cgtgtggtca gcgtcctcac cgttgtgcac caggactggc tgaacggcaa ggagtacaag   600
tgcaaggtct ccaacaaagg cctcccagcc ccatcgaga aaaccatctc caaaaccaaa    660
gggcagcccc gagaaccaca ggtgtacacc ctgcccccat cccgggagga gatgaccaag   720
aaccaggtca gcctgacctg cctggtcaaa ggcttctacc ccagcgacat cgccgtggag   780
tgggagagca atgggcagcc ggagaacaac tacaagacca cacctcccat gctggactcc   840
gacggctcct tcttcctcta cagcaagctc accgtggaca agagcaggtg gcagcagggg   900

```
aacgtcttct catgctccgt gatgcatgag gctctgcaca accactacac gcagaagagc      960
ctctccctgt ctccgggtaa atgataa                                          987

<210> SEQ ID NO 88
<211> LENGTH: 1013
<212> TYPE: DNA
<213> ORGANISM: Artificial Sequence
<220> FEATURE:
<223> OTHER INFORMATION: R1-1kb-R2

<400> SEQUENCE: 88
ggcccaggcg gcctcagcta gcaccaaggg cccatcggtc ttccccctgg cgccctgctc       60
caggagcacc tccgagagca cagcggccct gggctgcctg gtcaaggact acttccccga      120
accggtgacg gtgtcgtgga actcaggcgc tctgaccagc ggcgtgcaca ccttcccagc      180
tgtcctacag tcctcaggac tctactccct cagcagcgtg gtgaccgtgc cctccagcaa      240
cttcggcacc cagacctaca cctgcaacgt agatcacaag cccagcaaca ccaaggtgga      300
caagacagtt gagcgcaaat gttgtgtcga gtgcccaccg tgcccagcac cacctgtggc      360
aggaccgtca gtcttcctct tccccccaaa acccaaggac accctcatga tctcccggac      420
ccctgaggtc acgtgcgtgg tggtggacgt gagccacgaa gaccccgagg tccagttcaa      480
ctggtacgtg gacggcgtgg aggtgcataa tgccaagaca aagccacggg aggagcagtt      540
caacagcacg ttccgtgtgg tcagcgtcct caccgttgtg caccaggact ggctgaacgg      600
caaggagtac aagtgcaagg tctccaacaa aggcctccca gcccccatcg agaaaaccat      660
ctccaaaacc aaagggcagc cccgagaacc acaggtgtac accctgcccc catcccggga      720
ggagatgacc aagaaccagg tcagcctgac ctgcctggtc aaaggcttct accccagcga      780
catcgccgtg gagtgggaga gcaatgggca gccggagaac aactacaaga ccacacctcc      840
catgctggac tccgacggct ccttcttcct ctacagcaag ctcaccgtgg acaagagcag      900
gtggcagcag gggaacgtct tctcatgctc cgtgatgcat gaggctctgc acaaccacta      960
cacgcagaag agcctctccc tgtctccggg taaatgataa ggccacatag gcc           1013

<210> SEQ ID NO 89
<211> LENGTH: 72
<212> TYPE: DNA
<213> ORGANISM: Artificial Sequence
<220> FEATURE:
<223> OTHER INFORMATION: Connexon with a length of  72bp

<400> SEQUENCE: 89
aggccgagga atttaaaatg aaatacctat tgcctacggc agccgctgga ttgttattac       60
ttgcggccca ac                                                           72

<210> SEQ ID NO 90
<211> LENGTH: 85
<212> TYPE: DNA
<213> ORGANISM: Artificial Sequence
<220> FEATURE:
<223> OTHER INFORMATION: R3-connexon-R4 (72bp)

<400> SEQUENCE: 90
ggccacatag gccgaggaat ttaaaatgaa atacctattg cctacggcag ccgctggatt       60
gttattactt gcggcccaac cggcc                                             85

<210> SEQ ID NO 91
```

```
<211> LENGTH: 1012
<212> TYPE: DNA
<213> ORGANISM: Artificial Sequence
<220> FEATURE:
<223> OTHER INFORMATION: R5-1kb-R6

<400> SEQUENCE: 91
ggcccaaccg gcctcagcta gcaccaaggg cccatcggtc ttccccctgg cgccctgctc      60
caggagcacc tccgagagca cagcggccct gggctgcctg gtcaaggact acttccccga     120
accggtgacg gtgtcgtgga actcaggcgc tctgaccagc ggcgtgcaca ccttcccagc     180
tgtcctacag tcctcaggac tctactccct cagcagcgtg gtgaccgtgc cctccagcaa     240
cttcggcacc cagacctaca cctgcaacgt agatcacaag cccagcaaca ccaaggtgga     300
caagacagtt gagcgcaaat gttgtgtcga gtgcccaccg tgcccagcac cacctgtggc     360
aggaccgtca gtcttcctct tccccccaaa acccaaggac accctcatga tctcccggac     420
ccctgaggtc acgtgcgtgg tggtggacgt gagccacgaa gaccccgagg tccagttcaa     480
ctggtacgtg gacggcgtgg aggtgcataa tgccaagaca aagccacggg aggagcagtt     540
caacagcacg ttccgtgtgg tcagcgtcct caccgttgtg caccaggact ggctgaacgg     600
caaggagtac aagtgcaagg tctccaacaa aggcctccca gcccccatcg agaaaaccat     660
ctccaaaacc aaagggcagc ccgagaacac aggtgtac accctgcccc catcccggga     720
ggagatgacc aagaaccagg tcagcctgac ctgcctggtc aaaggcttct accccagcga     780
catcgccgtg gagtgggaga gcaatgggca gccggagaac aactacaaga ccacacctcc     840
catgctggac tccgacggct ccttcttcct ctacagcaag ctcaccgtgg acaagagcag     900
gtggcagcag gggaacgtct tctcatgctc cgtgatgcat gaggctctgc acaaccacta     960
cacgcagaag agcctctccc tgtctccggg taaatgataa cgtctcctca gc            1012

<210> SEQ ID NO 92
<211> LENGTH: 61
<212> TYPE: DNA
<213> ORGANISM: Artificial Sequence
<220> FEATURE:
<223> OTHER INFORMATION: Forward primer of pUC19 vector mutation

<400> SEQUENCE: 92
atgacggtgt taacctctga cacatgcagc tcccggagaa ggtcacagct tgtctgtaag      60
c                                                                     61

<210> SEQ ID NO 93
<211> LENGTH: 57
<212> TYPE: DNA
<213> ORGANISM: Artificial Sequence
<220> FEATURE:
<223> OTHER INFORMATION: Reverse primer of pUC19 vector mutation

<400> SEQUENCE: 93
gtcagaggtt aacaccgtca tcaccgaaac gcgcgacacg aaagggcctc gtgatac         57

<210> SEQ ID NO 94
<211> LENGTH: 90
<212> TYPE: DNA
<213> ORGANISM: Artificial Sequence
<220> FEATURE:
<223> OTHER INFORMATION: Connexon with a length of 90bp

<400> SEQUENCE: 94
aggccttcta gataattaat taggaggaat ttaaaatgaa ataccttattg cctacggcag     60
```

```
ccgctggatt gttattactt gcggcccaac                                      90
```

<210> SEQ ID NO 95
<211> LENGTH: 103
<212> TYPE: DNA
<213> ORGANISM: Artificial Sequence
<220> FEATURE:
<223> OTHER INFORMATION: R3-connexon-R4 (90bp)

<400> SEQUENCE: 95

```
ggccacatag gccttctaga taattaatta ggaggaattt aaaatgaaat acctattgcc     60
tacggcagcc gctggattgt tattacttgc ggcccaaccg gcc                      103
```

<210> SEQ ID NO 96
<211> LENGTH: 44
<212> TYPE: DNA
<213> ORGANISM: Artificial Sequence
<220> FEATURE:
<223> OTHER INFORMATION: Forward primer of 90bp connexon

<400> SEQUENCE: 96

```
agtgttaata ggccacatag gccttctaga taattaatta ggag                     44
```

<210> SEQ ID NO 97
<211> LENGTH: 42
<212> TYPE: DNA
<213> ORGANISM: Artificial Sequence
<220> FEATURE:
<223> OTHER INFORMATION: Forward primer of 90bp connexon

<400> SEQUENCE: 97

```
ccttctagat aattaattag gaggaattta aaatgaaata cc                       42
```

<210> SEQ ID NO 98
<211> LENGTH: 29
<212> TYPE: DNA
<213> ORGANISM: Artificial Sequence
<220> FEATURE:
<223> OTHER INFORMATION: Reverse primer of 90bp connexon

<400> SEQUENCE: 98

```
acctcggcca tggccggttg ggccgcaag                                      29
```

<210> SEQ ID NO 99
<211> LENGTH: 13
<212> TYPE: DNA
<213> ORGANISM: Artificial Sequence
<220> FEATURE:
<223> OTHER INFORMATION: Recognition sequence of SfiI
<220> FEATURE:
<221> NAME/KEY: misc_feature
<222> LOCATION: (5)..(9)
<223> OTHER INFORMATION: n is a, c, g, or t

<400> SEQUENCE: 99

```
ggccnnnnng gcc                                                       13
```

<210> SEQ ID NO 100
<211> LENGTH: 12
<212> TYPE: DNA
<213> ORGANISM: Artificial Sequence
<220> FEATURE:
<223> OTHER INFORMATION: Recognition sequence of BsmBI and Esp3I
<220> FEATURE:
<221> NAME/KEY: misc_feature
<222> LOCATION: (7)..(12)

```
<223> OTHER INFORMATION: n is a, c, g, or t

<400> SEQUENCE: 100
cgtctcnnnn nn                                                                12
```

METHOD FOR PREPARING PHAGE LIBRARY

CROSS REFERENCE TO RELATED APPLICATION

This application is a National Stage Application and claims priority under 35 U.S.C. § 371 to Patent Cooperation Treaty application PCT/CN2020/085706, filed Apr. 20, 2020, which claims the benefit of Chinese Application CN201910327739.6, filed Apr. 22, 2019. Priority is claimed to these applications and the disclosures of these prior applications are considered part of the disclosure of this application and to the extent allowed the entire contents of the aforementioned applications are incorporated herein.

FIELD OF THE INVENTION

The present application relates to the biomedical field, in particular to a method for producing a phage library displaying antibodies or antibody fragments.

BACKGROUND

There are some methods for preparing a phage library in the art, but these methods have some defects. For example, the library capacity is too small (e.g., it is hard to obtain libraries with a capacity of more than $10^9$), and the diversity of library is insufficient to meet the requirements for screening high-quality antibodies. At the same time, in order to expand the library capacity, it is required to accumulate a plurality of smaller libraries. It is not only required to take several years, but also difficult to ensure the consistency among these smaller libraries to control the quality of the obtained libraries. Moreover, when constructing a library by the existing methods, it is difficult to perform convenient and reliable quality control during the preparation of library. Usually, the quality cannot be known until the library is established, and therefore the process is at high risk and has high probability of failure.

Moreover, the library built in accordance with the existing method has high cost, long period, and serious quality decline after long-term storage, and therefore it is hard to meet the requirement of industrial mass production.

Hence, there is an urgent need for methods of preparing large-capacity phage library that can meet the requirement of industrial mass production, have controlled quality, and are convenient to operate.

SUMMARY OF THE INVENTION

The present application provides a method for producing a phage library displaying an antibodiy or an antibody fragment, as well as a phage library produced in accordance with the method, and a method of selecting an antibodiy or an antibody fragment by means of the phage library. The method for producing a phage library displaying an antibodiy or an antibody fragment described in the present application has at least one of the following properties: 1) the probability of introducing mutations caused by PCR is effectively reduced; the phage library described in the present application is not constructed by adopting the overlapping PCR strategy used by conventional antibody library construction method in the art, each component used for constructing the phage library can be amplified by PCR only once, and then connected to desired components to obtain the phage library of Fab; 2) it can meet the requirements of industrialized mass production; 3) it can easily carry out quality control; quality control can be independently and conveniently performed in each step required for constructing the phage library of the present application; at the same time, after the phage library of the present application is obtained, it can be simply and conveniently subject to quality analysis (e.g., by gene sequencing or soluble Fab expression analysis); 4) the preparation process is simple and fast; the phage library of the present application can be constructed with the recognition site(s) of specific restriction endonuclease, which can both ensure directed connection, and prevent mis-connection; during the connection, the molecular numbers of each component fragment can be controlled to 1:1, so as to improve the connection and conversion efficiency; at the same time, by use of strategies of constructing bacterial libraries such as light chain component bacterial libraries, the connection and conversion efficiency of each antibody or its fragments are improved (e.g., the obtained connection products have a conversion efficiency of greater than about $10^9$/µg); by obtaining connexon component plasmids, it ensures that the obtained released connexon has an appropriate and complete adhesive terminal, so that the conversion efficiency is improved; in addition, the phage library of the present application can be cultured either by dish culture or by liquid culture; 5) the produced library has a large capacity and a good diversity, so as to facilitate quickly and efficiently selecting antibodies or antigen binding fragments thereof 6) It is highly specific; the phage library of the present application is not constructed with degenerate primers used in conventional methods in the art, thereby avoiding any error caused by the degenerate primers; at the same time, the primers for use in construction of the phage library of the present application needs relatively high PCR annealing temperature, which can increase the binding specificity between these primers and their amplified target fragments; and 7) it is expandable and easy to preserve; bacterial libraries including light chain component bacterial libraries and bacteria containing connexon component plasmids can be stored at −80° C. for a long term, and can be used at any time if required (e.g., only two days are required to obtain the phage library of the present application), and different types and proportions can be mixed as needed.

In an aspect, the present application provides a method for producing a library displaying an antibodiy or an antibody fragment including: 1) providing a first polynucleotide containing LC, a second polynucleotide containing connexon, and a third polynucleotide containing HC, wherein the LC includes a nucleic acid sequence encoding the light chain or the light chain fragment of the antibody or the antibody fragment, and the HC includes a nucleic acid sequence encoding the heavy chain or the heavy chain fragment of the antibody or the antibody fragment; 2) introducing the first polynucleotide into a first bacterium to obtain a light chain component bacterial library, introducing the second polynucleotide into a second bacterium to obtain a connexon component bacterium, and introducing the third polynucleotide into a third bacterium to obtain a heavy chain component bacterial library; 3) obtaining a light chain component plasmid including the LC from the light chain component bacterial library, obtaining a connexon component plasmid including the connexon from the connexon component bacteria, and obtaining a heavy chain component plasmid including the HC from the heavy chain component bacterial library; 4) obtaining a released LC from the light chain component plasmid, obtaining a released connexon from the connexon component plasmid, and obtaining a released HC from the heavy chain component plasmid; 5) providing a display vector, and obtaining a released display vector fragment from the display vector; 6) connecting the released LC, the released connexon, the released HC, and the released display vector fragment to form a connection product for display; 7) introducing the connection product for display into a fourth bacterium to obtain the display bacterial library of the antibody or the antibody fragment; and 8) preparing a phage library displaying the antibody or the antibody fragment with the display bacterial library.

In some embodiments, the connection product for display in the 6) can express the light chain or the light chain fragment and the heavy chain or the heavy chain fragment in accordance with reading frames under a condition suitable for expression of an antibodiy or an antibody fragment.

In some embodiments, the first polynucleotide, the second polynucleotide and the third polynucleotide are all linear nucleic acid molecules.

In some embodiments, the nucleic acid sequence encoding the heavy chain or the heavy chain fragment and the nucleic acid sequence encoding the light chain or the light chain fragment are located in different reading frames.

In some embodiments, the connexon includes the nucleic acid sequence encoding a signal peptide pelB or a fragment thereof. In some embodiments, the connexon has a length of about 50 to about 200 bases.

In some embodiments, in the connection product for display in the 6), the LC is located upstream of the connexon, and the connexon is located upstream of the HC.

In some embodiments, the 2) includes cryopreserving the light chain component bacterial library and/or the heavy chain component bacterial library.

In some embodiments, the 7) includes cryopreserving the display bacterial library.

In some embodiments, the 8) includes thawing and culturing the cryopreserved display bacterial library, and constructing the phage library with the cultured display bacterial library.

In some embodiments, the first polynucleotide includes a structure of R1-LC-R2 in the 5' to 3' direction, the second polynucleotide includes a structure of R3-connexon-R4 in the 5' to 3' direction, the third polynucleotide includes a structure of R5-HC-R6 in the 5' to 3' direction, and the display vector includes a structure of R7-display vector fragment-R8 in the 5' to 3' direction, wherein the R1, R2, R3, R4, R5, R6, R7 and R8 are the restriction endonuclease recognition sites.

In some embodiments, a terminal produced by cleaving the R2 with a restriction endonuclease can recognize and be connected to a terminal produced by cleaving the R3 with a restriction endonuclease, vice versa; and cannot recognize or be connected to a terminal produced by cleaving any one of the R1, R4, R5, R6, R7 and R8 with a restriction endonuclease, vice versa.

In some embodiments, a terminal produced by cleaving the R4 with a restriction endonuclease can recognize and be connected to a terminal produced by cleaving the R5 with a restriction endonuclease, vice versa; and cannot recognize or be connected to a terminal produced by cleaving any one of the R1, R2, R3, R6, R7 and R8 with a restriction endonuclease, vice versa.

In some embodiments, a terminal produced by cleaving the R6 with a restriction endonuclease can recognize and be connected to a terminal produced by cleaving the R7 with a restriction endonuclease, vice versa; and cannot recognize or be connected to a terminal produced by cleaving any one of the R1, R2, R3, R4, R5 and R8 with a restriction endonuclease, vice versa.

In some embodiments, a terminal produced by cleaving the R8 with a restriction endonuclease can recognize and be connected to a terminal produced by cleaving the R1 with a restriction endonuclease, vice versa; and cannot recognize or be connected to a terminal produced by cleaving any one of the R2, R3, R4, R5, R6 and R7 with a restriction endonuclease, vice versa.

In some embodiments, a terminal produced by cleaving any one of R1, R2, R3, R4, R5, R6, R7 and R8 with s restriction endonuclease is a non-palindrome sequence.

In some embodiments, two or more of the R1, R2, R3, R4, R5, R6, R7 and R8 can be recognized and cleaved with the same restriction endonuclease.

In some embodiments, the R2 is identical to the R3. In some embodiments, the R4 is identical to the R5. In some embodiments, the R6 is identical to the R7. In some embodiments, the R8 is identical to the R1.

In some embodiments, the R1, R2, R3, R4, R5 and R8 can be recognized and cleaved with the same restriction endonuclease. In some embodiments, the R6 and R7 can be recognized and cleaved with the same restriction endonuclease.

In some embodiments, the restriction endonuclease is selected from the group consisting of SfiI, BsmBI and Esp3I. In some embodiments, the R1, R2, R3, R4, R5 and R8 can be recognized and cleaved with SfiI. In some embodiments, the R6 and R7 can be recognized and cleaved with BsmBI and/or Esp3I.

In some embodiments, the R1 includes a nucleic acid sequence as shown in SEQ ID NO: 1.

In some embodiments, the R2 includes a nucleic acid sequence as shown in SEQ ID NO: 2.

In some embodiments, the R3 includes a nucleic acid sequence as shown in SEQ ID NO: 2.

In some embodiments, the R4 includes a nucleic acid sequence as shown in SEQ ID NO: 3.

In some embodiments, the R5 includes a nucleic acid sequence as shown in SEQ ID NO: 3.

In some embodiments, the R6 includes a nucleic acid sequence as shown in SEQ ID NO: 4.

In some embodiments, the R7 includes a nucleic acid sequence as shown in SEQ ID NO: 4.

In some embodiments, the R8 includes a nucleic acid sequence as shown in SEQ ID NO: 1.

In some embodiments, the light chain or the light chain fragment includes a light chain variable region moiety and/or a light chain constant region moiety. In some embodiments, the heavy chain or the heavy chain fragment includes a heavy chain variable region moiety and/or a heavy chain constant region moiety. In some embodiments, the antibody or the fragment thereof includes Fab, Fab', (Fab)2 and/or (Fab')2.

In some embodiments, the connection product for display in the 7) has a connection and conversion efficiency of at least $10^8$ clones/μg polynucleotide.

In some embodiments, the 2) includes digesting the first polynucleotide with a restriction endonuclease recognizing R1 and R2, connecting the digested first polynucleotide to a light chain storage vector fragment to form a light chain storage connection product, and introducing the light chain storage connection product into the first bacterium to obtain the light chain component bacterial library; wherein the light chain storage vector includes the R1 and R2, and the light chain storage vector fragment is obtained by digesting the light chain storage vector with a restriction endonuclease recognizing R1 and R2.

In some embodiments, the light chain storage vector is derived from the pUC vector. In some embodiments, the pUC vector is or is derived from a pUC19 vector. In some embodiments, the pUC vector is or is derived from a pMD19-T vector.

In some embodiments, the restriction endonuclease recognizing R1 and R2 includes SfiI.

In some embodiments, the 2) includes digesting the third polynucleotide with a restriction endonuclease recognizing R5 and R6, connecting the digested third polynucleotide to a heavy chain storage vector fragment to form a heavy chain storage connection product, and introducing the heavy chain storage connection product into the third bacterium to obtain the heavy chain component bacterial library; wherein the heavy chain storage vector includes the R5 and R6, and the heavy chain storage vector fragment is obtained by digesting the heavy chain storage vector with a restriction endonuclease recognizing R5 and R6. In some embodiments, the heavy chain storage vector is derived from a pUC vector. In some embodiments, the pUC vector is or is derived from a pUC19 vector. In some embodiments, the pUC vector is or is derived from a pMD19-T vector.

In some embodiments, the heavy chain storage vector includes and only includes a recognition site of BsmBI.

In some embodiments, the restriction endonuclease recognizing R5 and R6 includes SfiI, BsmBI and/or Esp3I.

In some embodiments, the 2) includes connecting the second polynucleotide to a vector fragment to form a connexon storage vector, and introducing the connexon storage vector into the second bacterium to obtain the connexon component bacterium. In some embodiments, the connexon storage vector includes the R3 and R4. In some embodiments, the vector fragment for constructing the connexon storage vector is derived from a pUC vector. In some embodiments, the pUC vector is or is derived from a pUC19 vector. In some embodiments, the pUC vector is or is derived from a pMD19-T vector.

In some embodiments, the 4) includes digesting the light chain component plasmid with a restriction endonuclease recognizing R1 and R2, so as to obtain the released LC. In some embodiments, the restriction endonuclease recognizing R1 and R2 includes SfiI.

In some embodiments, the 4) includes digesting the heavy chain component plasmid with a restriction endonuclease recognizing R5 and R6, so as to obtain the released HC. In some embodiments, the restriction endonuclease recognizing R5 and R6 includes SfiI, BsmBI and/or Esp3I.

In some embodiments, the 4) includes digesting the connexon storage vector with a restriction endonuclease recognizing R3 and R4, so as to obtain the released connexon. In some embodiments, the 4) includes obtaining an amplification product from the connexon storage vector, and the amplification product includes the connexon, the R3 and the R4; and digesting the amplification product with a restriction endonuclease recognizing R3 and R4, so as to obtain the released connexon. In some embodiments, the restriction endonuclease recognizing R3 and R4 includes SfiI.

In some embodiments, the 5) includes digesting the display vector with a restriction endonuclease recognizing R7 and R8 to release the display vector fragment. In some embodiments, the restriction endonuclease recognizing R7 and R8 includes SfiI, BsmBI and/or Esp3I.

In some embodiments, the display vector is derived from a pComb3x vector.

In some embodiments, three different digested fragments are obtained after the display vector is digested with a restriction endonuclease recognizing R1, R2, R3, R4, R5 and R8. In some embodiments, the restriction endonuclease recognizing R1, R2, R3, R4, R5 and R8 includes SfiI. In some embodiments, after digesting the display vector with a restriction endonuclease recognizing R6 and R7, the display vector is linearized. In some embodiments, the restriction endonuclease recognizing R6 and R7 includes BsmBI and/or Esp3I.

In some embodiments, four different digested fragments are obtained after the display vector is digested with a restriction endonuclease recognizing R1, R2, R3, R4, R5 R6, R7 and R8. In some embodiments, the restriction endonuclease recognizing R1, R2, R3, R4, R5, R6, R7 and R8 includes SfiI, BsmBI and/or Esp3I.

In some embodiments, the 2) includes detecting samples from the light chain component bacterial library, the connexon component bacterium and/or the heavy chain component bacterial library to determine a library capacity and/or quality of the light chain component bacterial library, the connexon component bacterium and/or the heavy chain component bacterial library.

In some embodiments, the light chain component bacterial library includes at least $10^6$ different clones.

In some embodiments, the heavy chain component bacterial library includes at least $10^7$ different clones.

In some embodiments, an effective cloning proportion in the light chain component bacterial library is at least about 70%.

In some embodiments, an effective cloning proportion in the heavy chain component bacterial library is at least about 70%.

In some embodiments, the 2) includes calculating a capacity and/or quality of the display bacterial library based on the library capacity of the light chain component bacterial library and/or the heavy chain component bacterial library, the connexon component bacterium and/or mass.

In some embodiments, the display bacterial library includes at least $10^{10}$ different clones.

In some embodiments, an effective cloning proportion in the display bacterial library is at least about 70%.

In some embodiments, the first polynucleotide and the third polynucleotide are obtained from a sample material. In some embodiments, the sample material includes a sample material derived from peripheral blood lymphocyte sample. In some embodiments, the peripheral blood lymphocyte is human peripheral blood lymphocyte. In some embodiments, the sample material includes total RNA and/or mRNA derived from the sample.

In some embodiments, the 8) includes contacting the display bacterial library with a helper phage to prepare the phage library.

In another aspect, the present application provides a phage library produced by the method as described. In some embodiments, the phage library includes at least $10^{10}$ different clones. In some embodiments, the phage library can display at least $10^{10}$ types of different antibodies or antibody fragments.

In another aspect, the present application provides a method for selecting an antibodiy or an antibody fragment, including using the phage library.

Persons skilled in the art can easily recognize other aspects and advantages of the present application from the following detailed description. The following detailed description only shows and describes exemplary embodiments of the present application. As persons skilled in the art will appreciate, the contents of the present application enable persons skilled in the art to make modifications to the disclosed embodiments without departing the spirit and scope of the invention involved in the present application. Correspondingly, the accompany drawings and description in the specification of the present application are only illustrative, rather than restrictive.

BRIEF DESCRIPTION OF DRAWINGS

The specific features of the invention involved in the present application are shown in the appended claims. By referring to the exemplary embodiments as detailedly described below and the accompanying drawings, the features and advantages of the invention involved in the present application can be better understood. The accompany drawings are briefly described as follows:

DETAILED DESCRIPTION OF THE EMBODIMENTS

Figure 1:
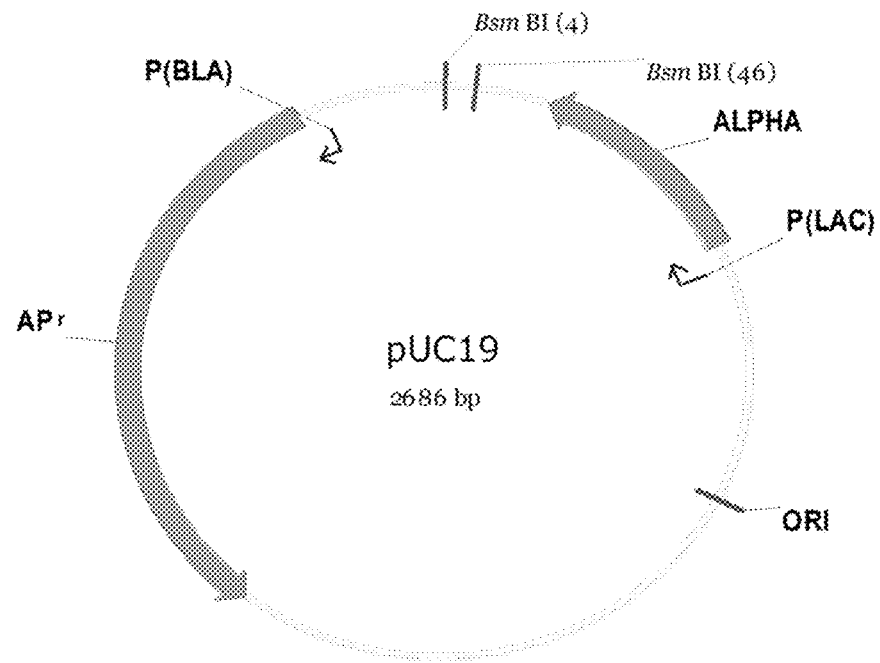
FIG. 1 shows a schematic diagram of pUC19 vector.
Figure 2:
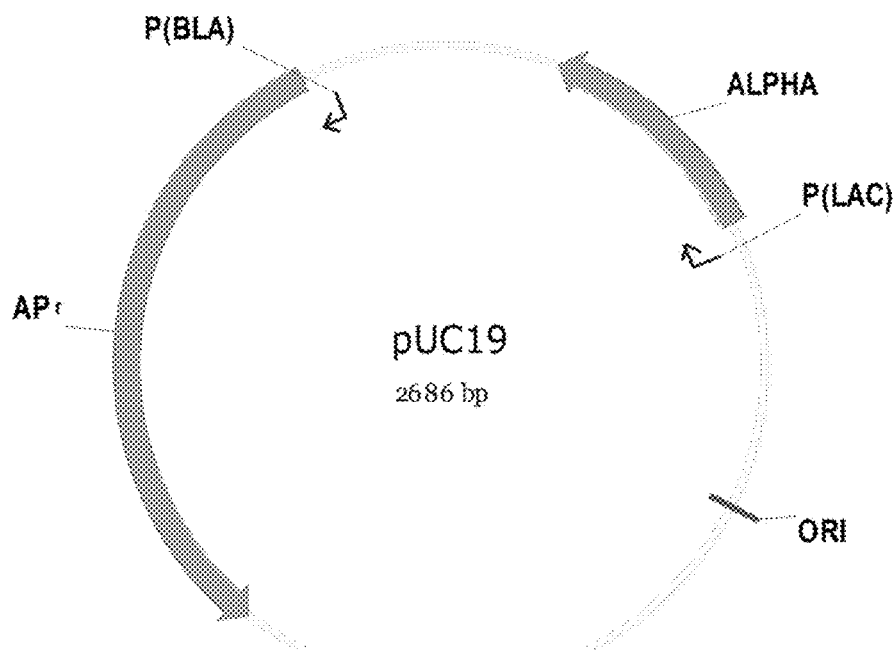
FIG. 2 shows a schematic diagram of modified pUC19 vector of the present application.

Hereinafter the embodiments of the invention of the application are described by specific examples. Those skilled in the art can easily understand other advantages and effects of the invention of the present application from the disclosure in the description.

In the present application, the term "phage library" generally refers to a polynucleotide library capable of displaying various recombinant polypeptides in phages. In some cases, the phage library may further include a combination of phages transfected with a polynucleotide library. In the present application, the library may refer to a collection or mixture of diversified polynucleotides including polynucleotides encoding various recombinant polypeptides. For example, the polynucleotide library collection may include at least $10^6$, $10^7$, $10^8$, $10^9$, $10^{10}$, $10^{11}$, $10^{12}$, $10^{13}$, $10^{14}$, $10^{15}$ or more types of different polynucleotides. The polynucleotides in the phage library may be derived from single species (e.g., mammals, such as, human beings), or tissues, organs, and/or cells thereof. The library may include polynucleotides of common genus. For example, the genus may be polynucleotides encoding a certain type or class of immunoglobulin subunit polypeptides. For example, the polynucleotide may encode a light chain or a light chain fragment of the antibody. For example, the polynucleotide may encode a heavy chain or a heavy chain fragment of the antibody.

In the present application, the term "antibody" generally refers to a polypeptide molecule capable of specifically recognizing and/or neutralizing a specific antigen. Basic tetra-stranded antibody unit is a heterotetrameric glycoprotein composed of two identical light chains and two identical heavy chains. In the case of IgG, each L chain is connected to an H chain via a covalent disulfide bond, while two H chains are connected with each other via one or more disulfide bonds, in which the number of the disulfide bonds depends on the isotype of the H chain. Each H or L chain further has regularly spaced intrachain disulfide bonds. Each H chain has a variable domain (VH) at the N-terminal, followed by three (for each α or γ chain) or four (for μ or ε isotype) constant domains (CH).

In the present application, the term "antibody fragment" generally refers to a part of an intact antibody. For example, the antibody fragment can include an antigen binding region and/or an antibody variable region of an intact antibody. The antibody fragment may be obtained by a chemical method and/or a genetic engineering method. For example, the antibody fragment may be produced by digesting the antibody with proteases including pepsin and papain. In the present application, the antibody fragment may be Fab.

In the present application, the term "Fab" generally refers to two identical antigen binding fragments obtained by digesting an antibody having an intact structure with pepsin (e.g., removing the Fc region and the hinge region). Fab can be composed of an intact light chain, a heavy chain variable region (VH) and a first constant domain of heavy chain (CH1). Each Fab may have a single antigen binding site.

In the present application, the term "connexon" generally refers to a reagent capable of connecting two or more polynucleotide molecules or fragments thereof. The connexon may be polynucleotide or a fragment thereof. In the present application, the connexon may vary in length. For example, the length of the connexon may be 40 bp or greater, 50 bp or greater, 60 bp or greater, 70 bp or greater, 80 bp or greater, 90 bp or greater, 100 bp or greater, 150 bp or greater, or 200 bp or greater.

In the present application, the term "LC" generally refers to a polypeptide including a nucleic acid sequence encoding a light chain or a light chain fragment of antibodies or antibody fragments. In the present application, the light chain or the light chain fragment may have a capacity of binding to the heavy chain of the same or similar antibody. In the present application, the light chain or the light chain fragment may include a light chain variable region (VL) and a light chain constant region (CL). The light chain constant region may be classified to a κ type and a λ type. The light chain further includes a light chain of a λ-variable region (V-λ) connected to a κ-constant region (C-κ) or a κ-variable region (V-κ) connected to a λ-constant region (C-λ). For example, the LC may be a polypeptide including a nucleic acid sequence encoding a light chain of an antibodiy or an antibody fragment.

In the present application, the term "HC" generally refers to a polypeptide including a nucleic acid sequence encoding a heavy chain or a heavy chain fragment of an antibodiy or an antibody fragment. In the present application, the heavy chain or the heavy chain fragment may have a capacity of binding to the light chain of the same or similar antibody. In the present application, the heavy chain or the heavy chain fragment may include a heavy chain variable region (VH) and a heavy chain constant region (CH). The heavy chain constant region may include a CH1 domain, a hinge region, a CH2 domain and a CH3 domain. In the cases of IgE, IgM and IgY, the heavy chain constant region may include a CH4 domain but do not include a hinge region. In the present application, the "heavy chain constant region" may be CH1, a hinge region, CH2, CH3, CH4 domain or any combination thereof. For example, the HC may be a polypeptide including a nucleic acid sequence encoding VH and CH1 of an antibodiy or an antibody fragment.

In the present application, the term "first polynucleotide" generally refers to a polynucleotide including an LC which may be a nucleic acid sequence including a light chain or a light chain fragment encoding the antibodies or the antibody fragments. In the present application, the first polynucleotide may further have a recognition site of endonuclease (e.g., the restriction endonuclease) at 5'-terminal and/or 3'-terminal. For example, the first polynucleotide may include, in the 5' to 3' direction, a structure of R1-LC-R2, wherein the R1, R2 may be the restriction endonuclease recognition sites. For example, by digestion with the endonuclease recognizing the endonuclease recognition site in the first polynucleotide (e.g., the restriction endonuclease recognizing R1 and R2, such as, SfiI), the digested first polynucleotide may include the LC.

In the present application, the term "light chain storage vector fragment" generally refers to fragments of the light chain storage vector obtained by digestion with the restriction endonuclease. In the present application, the restriction endonuclease recognition site(s) contained in the light chain storage vector may be correspondingly the same as the restriction endonuclease recognition site(s) contained in the first polynucleotide. For example, the light chain storage vector may include the R1 and the R2. In the present application, by digestion with the restriction endonuclease (e.g., the restriction endonuclease recognizing the R1 and the R2), the obtained light chain storage vector fragment may be connected to the digested first polynucleotide. In the present application, the light chain storage vector fragment may be derived from a pUC vector. For example, the pUC vector may be or be derived from a pUC19 vector; alternatively, e.g., the pUC vector may be or be derived from a pMD19-T vector.

In the present application, the term "light chain storage connection product" generally refers to a product formed by connecting the digested first polynucleotide to the light chain storage vector fragment. In the present application, the first polynucleotide and the light chain storage vector fragment may include the same restriction endonuclease recognition site(s), and may be connected with a ligase (e.g., a DNA ligase) to obtain the light chain storage connection product.

In the present application, the term "first bacterium" generally refers to bacterium for introducing or containing the first polynucleotide. The first bacterium may include the LC. In the present application, the first bacterium may be introduced into the light chain storage connection product. In the present application, the first bacterium can express, replicate and/or store (e.g., cryopreserve) the LC, the first polynucleotide and/or the light chain storage connection product.

In the present application, the term "light chain component bacterial library" generally refers to a bacterial library obtained by introducing the first polynucleotide into the first bacteria. In the present application, the light chain component bacterial library may be a bacterial library including nucleic acid sequences encoding the light chain or the light chain fragments of an antibodiy or an antibody fragment. In the present application, the light chain component bacterial library may include about $10^5$ to about $10^9$ (e.g., may include about $10^5$ to about $10^8$, about $10^5$ to about $10^7$, about $10^6$ to about $10^7$) nucleic acid sequences encoding various light chains or light chain fragments of antibodies or antibody fragments. In the present application, the light chain component bacterial library may include about $10^7$ to about $10^{12}$ (e.g., about $10^7$ to about $10^{11}$, about $10^7$ to about $10^{10}$, about $10^7$ to about $10^9$, about $10^7$ to about $10^8$) first bacteria.

In the present application, the term "second polynucleotide" generally refers to a polynucleotide including a connexon. In the present application, the second polynucleotide may further include recognition site(s) of endonuclease (e.g., the restriction endonuclease) located at 5'-terminal and/or 3'-terminal. For example, the first polynucleotide may include, in the 5' to 3' direction, a structure of R3-connexon-R4, wherein the R3, R4 may be the restriction endonuclease recognition sites. For example, after digestion with an endonuclease recognizing the endonuclease recognition site(s) in the second polynucleotide (e.g., the restriction endonuclease recognizing R3 and R4, such as, SfiI), the digested second polynucleotide may include the connexon.

In the present application, when used in combination with the second polynucleotide or the connexon, the term "vector fragment" generally refers to a vector fragment which is able to connect to the second polynucleotide. In the present application, the vector fragment may be derived from a pUC vector. For example, the pUC vector may be or be derived from a pUC19 vector; alternatively, for example, the pUC vector may be or be derived from a pMD19-T vector.

In the present application, the term "connexon storage vector" generally refers to a product formed by connecting the second polynucleotide to the vector fragment. In the present application, the restriction endonuclease recognition site(s) included in the connexon storage vector and the restriction endonuclease recognition site(s) included in the first polynucleotide may be correspondingly the same. For example, the connexon storage vector may include the R3 and the R4. In the present application, the connexon storage vector may include only one connexon.

In the present application, the term "second bacterium" generally refers to a bacterium for introducing or including the second polynucleotide. The second bacterium may include the connexon. In the present application, the second bacterium can be introduced into the connexon storage vector. In the present application, the second bacterium can express, replicate and/or store (e.g., cryopreserve) the connexon and/or the second polynucleotide.

In the present application, the term "connexon component bacterium" generally refers to a bacterium obtained by introducing the connexon storage vector into the second bacteria. In the present application, the connexon component bacterial may be a single species of bacteria. In the present application, the single species of connexon component bacterium may include only a single species of the connexons.

In the present application, the term "third polynucleotide" generally refers to a polynucleotide including an HC which may be a nucleic acid sequence encoding the heavy chain or the heavy chain fragment of the antibodies or the antibody fragments. In the present application, the third polynucleotide may further include recognition site(s) of endonucleases (e.g., the restriction endonuclease) at 5'-terminal and/or 3'-terminal. For example, the first polynucleotide may include, in the 5' to 3' direction, a structure of R5-HC-R6, wherein the R5, R6 may be the restriction endonuclease recognition sites. For example, after digestion with endonucleases recognizing the endonuclease recognition site(s) in the third polynucleotide (e.g., the restriction endonuclease recognizing R5, such as, SfiI; alternatively, e.g., the restriction endonuclease recognizing R6, such as, SfiI, BsmBI and Esp3I), the digested third polynucleotide may include the HC.

In the present application, the term "heavy chain storage vector fragment" generally refers to fragments of a heavy chain store vector digested with the restriction endonuclease. In the present application, the restriction endonuclease recognition site(s) included in the heavy chain storage vector and the restriction endonuclease recognition site(s) contained in the third polynucleotide may be correspondingly the same. For example, the heavy chain storage vector may include the R5 and the R6. In the present application, after digestion with the restriction endonuclease (e.g., the restriction endonuclease recognizing the R5 and the R6), the obtained heavy chain storage vector fragment may be connected to the digested third polynucleotide. In the present application, the heavy chain storage vector fragment may be derived from a pUC vector. For example, the pUC vector may be or be derived from a pUC19 vector; alternatively, for example, the pUC vector may be or be derived from a pMD19-T vector.

In the present application, the term "heavy chain storage connection product" generally refers to a product formed by connecting the digested third polynucleotide to the heavy chain storage vector fragment. In the present application, the third polynucleotide and the heavy chain storage vector fragment may include the same restriction endonuclease recognition site(s), and may be connected with a ligase (e.g., a DNA ligase) to obtain the heavy chain storage connection product.

In the present application, the term "third bacterium" generally refers to bacterium for introducing or including the third polynucleotide. The third bacterium may include the HC. In the present application, the third bacterium may be introduced into the heavy chain storage connection product. In the present application, the third bacterium can express, replicate and/or store (e.g., cryopreserve) the HC, the third polynucleotide and/or the heavy chain storage connection product.

In the present application, the term "heavy chain component bacterial library" generally refers to a bacterial library obtained by introducing the third polynucleotide into the third bacteria. In the present application, the heavy chain component bacterial library may be a bacterial library including nucleic acid sequences encoding the heavy chain or the heavy chain fragments of antibodies or antibody fragments. In the present application, the heavy chain component bacterial library may include about $10^5$ to about $10^9$ (e.g., about $10^5$ to about $10^8$, about $10^5$ to about $10^7$, about $10^6$ to about $10^7$) nucleic acid sequences encoding various heavy chains or heavy chain fragments of antibodies or antibody fragments. In the present application, the heavy chain component bacterial library may include about $10^7$ to about $10^{12}$ (e.g., about $10^7$ to about $10^{11}$, about $10^7$ to about $10^{10}$, about $10^7$ to about $10^9$, about $10^7$ to about $10^8$) third bacteria.

In the present application, the term "light chain component plasmid" generally refers to a plasmid obtained from bacterium of the light chain component bacterial library and containing the LC. In the present application, the light chain component plasmid may include the LC. For example, the light chain component plasmid may include the first polynucleotide. In the present application, the light chain component plasmid may include the restriction endonuclease recognition site(s), e.g., R1 and R2.

In the present application, the term "heavy chain component plasmid" generally refers to a plasmid obtained from bacterium of the heavy chain component bacterial library and containing the HC. In the present application, the heavy chain component plasmid may include the HC. For example, the heavy chain component plasmid may include the third polynucleotide. In the present application, the heavy chain component plasmid may include the restriction endonuclease recognition site(s), e.g., R5 and R6.

In the present application, the term "released LC" generally refers to the LC released after the light chain component plasmid is treated. In the present application, the treatment may be digestion. For example, it is feasible to select suitable restriction endonuclease(s) (e.g., the restriction endonuclease(s) recognizing R1 and R2) against the restriction endonuclease recognition site(s) in the light chain component plasmid, so that the LC is released and separated from the light chain component plasmid.

In the present application, the term "released connexon" generally refers to the connexon released after the connexon component plasmid is treated. In the present application, the treatment may be digestion. For example, it is feasible to select suitable restriction endonuclease(s) (e.g., the restriction endonuclease(s) recognizing R3 and R4) against the restriction endonuclease recognition site(s) in the connexon component plasmid, so that the connexon is released and separated from the connexon component plasmid. Alternatively, e.g., it may first take the connexon component plasmid as a template to amplify (e.g., by using PCR amplification) to include the second polynucleotide, followed by digesting the obtained amplification product. For example, it is feasible to select suitable restriction endonuclease(s) (e.g., the restriction endonuclease(s) recognizing the R3 and R4) against the restriction endonuclease recognition site(s) in the connexon component plasmid, so that the connexon is released and separated from the connexon component plasmid.

In the present application, the term "released HC" generally refers to the HC released after the heavy chain component plasmid is treated. In the present application, the treatment may be digestion. For example, it is feasible to select suitable restriction endonuclease(s) (e.g., the R5 and R6) against the restriction endonuclease recognition site(s) in the heavy chain component plasmid, so that the HC is released and separated from the heavy chain component plasmid.

In the present application, the term "released display vector fragment" generally refers to display vector fragments released after the display vector is treated. In the present application, the display vector may include, in the 5' to 3' direction, a structure of R7-display vector fragment-R8, wherein the R7 and R8 may be the restriction endonuclease. In the present application, the treatment may be digestion with restriction endonuclease. For example, it is feasible to select suitable restriction endonuclease(s) (e.g., R7 and R8) against the restriction endonuclease recognition site(s) in the display vector, so that the released display vector fragment is released and separated from the display vector.

In the present application, the term "connect (connected, connecting, connection)" generally refers to connecting two or more polynucleotide molecules together. For example, the connection may be achieved by a ligase (e.g., a DNA ligase). For example, the 3' terminal of a polynucleotide is connected to the 5' terminal of another polynucleotide, so as to form an intact polynucleotide molecule.

In the present application, the term "connection product for display" generally refers to a polynucleotide molecule including the released LC, the released connexon, the released HC and the released display vector fragment. In the present application, the connection product for display may be obtained by mixing the released LC, the released connexon, the released HC and the released display vector fragment in proportion.

In the present application, the "display" may refer to expressing a protein (e.g., antibody or antibody fragment, such as, Fab) encoded by the connection product for display in a cell including the connection product for display.

In the present application, the term "introduce (introducing, introduced, introduction)" generally refers to a process in which an exogenous polynucleotide is transferred or directed into a cell. The cell may be a host cell. The introduced cell includes primary cells of a subject and progeny cells. The cell may be a prokaryotic cell, e.g., a bacterial cell.

In the present application, the term "fourth bacterium" generally refers to bacterium for introducing or including the connection product for display, wherein the connection product for display includes the released LC, the released connexon, the released HC and the released display vector fragment. In the present application, the fourth bacterium may introduce the connection product for display by transformation. In the present application, the fourth bacterium can express the light chain or the light chain fragment of antibodies or antibody fragments encoded by the released LC; alternatively, it can express the heavy chain or the heavy chain fragment of antibodies or antibody fragments encoded by the released HC. In the present application, the fourth bacterium can express, replicate and/or store (e.g., cryopreserve) the antibodies or antibody fragments.

In the present application, the term "display bacterial library" generally refers to a bacterial library including the connection product for display. In the present application, the bacterial library for display may include the fourth bacterium. In the present application, the display bacterial library may include $10^{10}$ or more of various antibodies or antibody fragments.

In the present application, the term "signal peptide pelB" generally refers to a signal peptide of pectinase lyase. The signal peptide pelB is generally used in a prokaryotic expression system. For example, the GenBank Accession Number of the signal peptide pelB may be ABS75961.1.

In the present application, the term "restriction endonuclease" generally refers to an enzyme that cleaves double-stranded DNAs. The restriction endonuclease can produce a stick terminal with a protruding single stranded DNA, so that it can adhere to a DNA ligase. In the present application, the restriction endonuclease may play roles of recognition and restrictive digestion. For example, the cleavage site of the restriction endonuclease is at a certain distance from its recognition site. For example, the restriction endonuclease may be selected from the group consisting of SfiI, BsmBI and Esp3I.

In the present application, the term "linearize (linearized, linearizing, linearization)" generally means that the vector is in a linear shape, other than a closed ring. For example, after the vector is subject to digestion, the original circular structure of the vector is destroyed, so that a linearized vector is formed. For example, the vector (e.g., T vector) can produce a T terminal at the 3' terminal after being digested with a restrictive endonuclease. At that time, it may be connected to a PCR product with A terminal by the action of a T4 ligase, so that the PCR product is connected with a linearized vector.

In the present application, the term "clone" generally refers to the number of colonies. For example, the clone may be the number of colonies in the bacterial library (e.g., the light chain component bacterial library, the heavy chain component bacterial library, the display bacterial library and/or the phage library). In some cases, the clone may be the number of various colonies in the bacterial library. In some cases, the clone may be the number of progeny population generated by a single clone.

In the present application, the term "polynucleotide" generally refers to nucleotides, that is, at least two nucleotides connected together. The polynucleotide may be a polymer in any length, including, e.g., 200, 300, 500, 1000, 2000, 3000, 5000, 7000, 10,000, 100,000, or the like. The polynucleotide may include a phosphodiester linkage.

In the present application, the term "comprise (contain, including)" generally refers to inclusion of a clearly specified feature without exclusion of other elements.

In the present application, the term "about" generally refers to variation in a range of 0.5%-10% above or below the specified value, e.g., a variation in a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below the specified value.

In an aspect, the present application provides a method for producing a library displaying antibodies or antibody fragments, including: 1) providing a first polynucleotide containing LC, a second polynucleotide containing connexon, and a third polynucleotide containing HC, wherein the LC includes a nucleic acid sequence encoding the light chain or the light chain fragment of the antibodies or the antibody fragments, and the HC includes a nucleic acid sequence encoding the heavy chain or the heavy chain fragment of the antibodies or the antibody fragments; 2) introducing the first polynucleotide into first bacterium to obtain the light chain component bacterial library, introducing the second polynucleotide into second bacterium to obtain the connexon component bacterial library, and introducing the third polynucleotide into a third bacterium to obtain the heavy chain component bacterial library; 3) obtaining a light chain component plasmid including the LC from the light chain component bacterial library, obtaining a connexon component plasmid including the connexon from the connexon component bacterial library, and obtaining a heavy chain component plasmid including the HC from the heavy chain component bacterial library; 4) obtaining a released LC from the light chain component plasmid, obtaining a released connexon from the connexon component plasmid, and obtaining a released HC from the heavy chain component plasmid; 5) providing a display vector, and obtaining a released display vector fragment from the display vector; 6) connecting the released LC, the released connexon, the released HC, and the released display vector fragment to form a connection product for display; 7) introducing the connection product for display into a fourth bacterium to obtain the display bacterial library of the antibodies or the antibody fragments; and 8) preparing a phage library displaying the antibodies or the antibody fragments with the display bacterial library.

In the present application, the connection product for display in the 6) may express the light chain or the light chain fragment and the heavy chain or the heavy chain fragment in accordance with reading frames under conditions suitable for expression of antibodies or antibody fragments.

In the present application, the first polynucleotide, the second polynucleotide and the third polynucleotide may be all linear nucleic acid molecules.

In the present application, the nucleic acid sequence encoding the heavy chain or the heavy chain fragment and the nucleic acid sequence encoding the light chain or the light chain fragment may be located in different reading frames. In the present application, the reading frame may be a continuous nucleotide sequence starting from the start codon and ending at the stop codon, and does not include any promoter or terminator in its interior. For example, the reading frame can encode a protein or a polypeptide fragment.

In the present application, the connexon may include a nucleic acid sequence encoding the signal peptide pelB or a fragment thereof.

In the present application, the connexon may include a nucleic acid sequence encoding a fragment of the signal peptide pelB, while the other nucleic acid sequences encoding fragments of the signal peptide pelB may be further located in the R5. For example, the nucleotide at the 3' terminal of the nucleic acid sequence encoding the fragment of the signal peptide pelB may be located in the R5. For example, when the released connexon is connected to the released HC, the nucleic acid sequence encoding the fragment of the signal peptide pelB in the released connexon may be connected to the nucleic acid sequence encoding the fragment of the signal peptide pelB in the released HC, to form a nucleic acid sequence encoding the intact signal peptide pelB.

In the present application, the connexon may have a length of about 50 to about 200 bases. For example, the connexon may have a length of about 50 to about 200 bases, about 50 to about 180 bases, about 50 to about 160 bases, about 50 to about 140 bases, about 50 to about 120 bases, about 50 to about 100 bases, about 50 to about 90 bases, about 50 to about 80 bases, about 50 to about 75 bases, about 50 to about 70 bases, and about 50 to about 60 bases.

In the present application, in the connection product for display in the 6), the LC may be located upstream of the connexon, and the connexon may be located upstream of the HC. In the present application, the upstream may be the 5'-terminal of a nucleotide sequence.

In the present application, the 2) may include cryopreserving the light chain component bacterial library and/or the heavy chain component bacterial library. In the present application, the 7) may include cryopreserving the display bacterial library. In the present application, the cryopreserving may refer to storage at −18° C. or below, e.g., storage at −80° C. or below.

In the present application, the 8) may include thawing and culturing the cryopreserved display bacterial library, and constructing the phage library with the cultured display bacterial library.

In the present application, the first polynucleotide may include a structure of R1-LC-R2 in the 5' to 3' direction, the second polynucleotide includes a structure of R3-connexon-R4 in the 5' to 3' direction, the third polynucleotide may include a structure of R5-HC-R6 in the 5' to 3' direction, and the display vector may include a structure of R7-display vector fragment-R8 in the 5' to 3' direction, wherein the R1, R2, R3, R4, R5, R6, R7 and R8 are the restriction endonuclease recognition sites.

In the present application, a terminal produced by cleaving the R2 with the restriction endonuclease can recognize and be connected to a terminal produced by cleaving the R3 with the restriction endonuclease, vice versa; and cannot recognize or be connected to a terminal produced by cleaving any one of the R1, R4, R5, R6, R7 and R8 with the restriction endonuclease, vice versa. In the present application, the R2 may be identical to the R3.

In the present application, a terminal produced by cleaving the R4 with the restriction endonuclease can recognize and be connected to a terminal produced by cleaving the R5 with the restriction endonuclease, vice versa; and cannot recognize or be connected to a terminal produced by cleaving any one of the R1, R2, R3, R6, R7 and R8 with the restriction endonuclease, vice versa. In the present application, the R4 may be identical to the R5.

In the present application, a terminal produced by cleaving the R6 with the restriction endonuclease can recognize and be connected to a terminal produced by cleaving the R7 with the restriction endonuclease, vice versa; and cannot recognize or be connected to a terminal produced by cleaving any one of the R1, R2, R3, R4, R5 and R8 with the restriction endonuclease, vice versa. In the present application, the R6 may be identical to the R7.

In the present application, a terminal produced by cleaving the R8 with the restriction endonuclease can recognize and be connected to a terminal produced by cleaving the R1 with the restriction endonuclease, vice versa; and cannot recognize or be connected to a terminal produced by cleaving any one of the R2, R3, R4, R5, R6 and R7 with the restriction endonuclease, vice versa. In the present application, the R8 may be identical to the R1.

In the present application, a terminal produced by cleaving any one of R1, R2, R3, R4, R5, R6, R7 and R8 with the restriction endonuclease is a non-palindrome sequence.

Upon selection of the endonuclease recognition sites (e.g., R1, R2, R3, R4, R5, R6, R7 and R8), it is feasible to select a sequence which is not substantially contained in the antibody variable region (e.g., the light chain variable region or the heavy chain variable region) to maintain the integrity of the antibody variable region, so as to prevent the antibody gene pool from being damaged (e.g., degradation) during digestion. Moreover, the terminal formed by cleaving the nuclease recognition sites with the restriction endonuclease may be a non-palindrome sequence to avoid self-connection, thereby achieving the reduction of off-target connection. In addition, the selection of the endonuclease recognition sites may make the directional connection of a plurality of fragments be possible to improve the connection efficiency.

In the present application, two or more of the R1, R2, R3, R4, R5, R6, R7 and R8 (e.g., 2, 3, 4, 5, 6, 7 or 8) can be recognized and cleaved with the same restriction endonuclease.

For example, in the present application, the R1, R2, R3, R4, R5 and R8 can be recognized and cleaved with the same restriction endonuclease. For example, the R6 and R7 can be recognized and cleaved with the same restriction endonuclease. In some cases, the restriction endonuclease recognizing the R1, R2, R3, R4, R5 and R8 may be different from the restriction endonuclease recognizing the R6 and R7.

In the present application, the restriction endonuclease may be selected from the group consisting of SfiI, BsmBI and Esp3I. In the present application, the BsmBI and Esp3I may be isozymes which can recognize the same restriction endonuclease recognition site.

In the present application, e.g., the R1, R2, R3, R4, R5 and R8 can be recognized and cleaved by SfiI. In the present application, e.g., the R6 and R7 can be recognized and cleaved by BsmBI and/or Esp3I.

For example, SfiI can recognize a sequence consisting of 13 bases (from 5' to 3'): GGCCNNNN/NGGCC (SEQ ID NO:99), which can form a protruding sequence at 3'-terminal (overhang, such as, a single-stranded sequence containing 3 bases) after digestion, wherein N can represent any one of GATC bases. Therefore, there are 64 different sequences that can be recognized by SfiI.

For example, BsmBI and Esp3I can recognize a sequence consisting of 12 bases (from 5' to 3'): CGTCTCN (SEQ ID NO:100), which can form a protruding sequence at 5'-terminal (overhang, such as, a single-stranded sequence containing 4 bases), wherein N can represent any one of GATC bases. Therefore, there are 264 different sequences that can be recognized by BsmBI and Esp3I.

In the present application, the R1 may include a nucleic acid sequence as shown in SEQ ID NO: 1. In the present application, the R2 may include a nucleic acid sequence as shown in SEQ ID NO: 2. In the present application, the R3 may include a nucleic acid sequence as shown in SEQ ID NO: 2. In the present application, the R4 may include a nucleic acid sequence as shown in SEQ ID NO: 3. In the present application, the R5 may include a nucleic acid sequence as shown in SEQ ID NO: 3. In the present application, the R6 may include a nucleic acid sequence as shown in SEQ ID NO: 4. In the present application, the R7 may include a nucleic acid sequence as shown in SEQ ID NO: 4. In the present application, the R8 may include a nucleic acid sequence as shown in SEQ ID NO: 1.

In the present application, the light chain or the light chain fragment may include a light chain variable region moiety and/or a light chain constant region moiety. In the present application, the heavy chain or the heavy chain fragment may include a heavy chain variable region moiety and/or a heavy chain constant region moiety.

For example, the LC may include a polynucleotide encoding the light chain variable region VL of the light chain or the light chain fragment. For example, the first polynucleotide may include a polynucleotide encoding the light chain variable region VL of the light chain or the light chain fragment. The 5'-terminal of the first polynucleotide may be connected to the R1, and the 3'-terminal of the first polynucleotide may be connected to the R2; and the 5'-terminal of the light chain storage vector fragment may be connected to R3, and the 3'-terminal of the light chain storage vector fragment may be connected to the R8.

For example, the HC may include a polynucleotide encoding the heavy chain variable region VH and the CH1 of the heavy chain constant region of the heavy chain or the heavy chain fragment. For example, the third polynucleotide may include a polynucleotide encoding the heavy chain variable region VH and the CH1 of the heavy chain constant region of the heavy chain or the heavy chain fragment. The 5'-terminal of the third polynucleotide may be connected to the R5, and the 3'-terminal of the third polynucleotide may be connected to the R6; and the 5'-terminal of the heavy chain storage vector fragment may be connected to R7, and the 3'-terminal of the heavy chain storage vector fragment may be connected to the R4.

Alternatively, for example, the HC may include a polynucleotide encoding the heavy chain variable region VH of the heavy chain or the heavy chain fragment. For example, the third polynucleotide may include a polynucleotide encoding the heavy chain variable region VH of the heavy chain or the heavy chain fragment. At that time, the heavy chain storage vector fragment may include a polynucleotide encoding the CH1 of the heavy chain constant region of the heavy chain or the heavy chain fragment. The 5'-terminal of the third polynucleotide may be connected to the R5, and the 3'-terminal of the third polynucleotide may be connected to the R6; and the 5'-terminal of the heavy chain storage vector fragment may be connected to R7, and the 3'-terminal of the heavy chain storage vector fragment may be connected to the R4.

In the present application, the antibody or the fragment thereof may include Fab, Fab', (Fab)2 and/or (Fab')2.

In the present application, the connection product for display in the 7) may have a connection and conversion efficiency of at least $10^8$ clones/μg polynucleotide (e.g., at least $10^9$ clones/μg polynucleotide, at least $10^{10}$ clones/μg polynucleotide, at least $10^{11}$ clones/μg polynucleotide, and at least $10^{12}$ clones/μg polynucleotide).

In the present application, the 2) may include digesting the first polynucleotide with a restriction endonuclease recognizing the R1 and R2, connecting the digested first polynucleotide to a light chain storage vector fragment to form a light chain storage connection product, and introducing the light chain storage connection product into the first bacterium to obtain the light chain component bacterial library; wherein the light chain storage vector includes the R1 and R2, and the light chain storage vector fragment is obtained by digesting the light chain storage vector with the restriction endonuclease recognizing the R1 and R2.

In the present application, the LC may have a length of greater than about 600 bp. For example, it may be greater than about 650 bp, greater than about 680 bp, and greater than about 700 bp. In the present application, the first polynucleotide may have a length of greater than about 600 bp. For example, it may be greater than about 650 bp, greater than about 680 bp, and greater than about 700 bp. In the present application, the light chain storage vector fragment may have a length of greater than about 900 bp, e.g., greater than about 1000 bp, greater than about 1500 bp, greater than about 1800 bp, and greater than about 2100 bp. In the present application, the length of the light chain storage vector fragment may be substantially different from the length of the LC. For example, the length of the light chain storage vector fragment may be substantially distinguished from the length of the LC by means of polyacrylamide gel electrophoresis (PAGE).

In the present application, the light chain storage vector may be derived from any vector, such as, any vector that may be amplified and/or easy to store. In some cases, the vector used as the light chain storage vector may have properties including high copies, low molecular weight, etc. For example, the light chain storage vector may be a pUC vector. In the present application, the pUC vector may be a pUC19 vector (the schematic structural view of which may be as shown in FIG. 1) or be derived from the pUC19 vector. In the present application, the pUC vector may be or be derived from a pMD19-T vector.

In the present application, the restriction endonuclease recognizing the R1 and R2 may include SfI.

In the present application, the 2) may include digesting the third polynucleotide with a restriction endonuclease recognizing the R5 and R6, connecting the digested third polynucleotide to a heavy chain storage vector fragment to form a heavy chain storage connection product, and introducing the heavy chain storage connection product into the third bacterium to obtain the heavy chain component bacterial library; wherein the heavy chain storage vector includes the R5 and R6, and the heavy chain storage vector fragment is obtained by digesting the heavy chain storage vector with the restriction endonuclease recognizing the R5 and R6.

In the present application, the HC may have a length of greater than about 320 bp. For example, it may be greater than about 350 bp, greater than about 380 bp, and greater than about 400 bp. In the present application, the third polynucleotide may have a length of greater than about 320 bp. For example, it may be greater than about 350 bp, greater than about 380 bp, and greater than about 400 bp. In the present application, the heavy chain storage vector fragment may have a length of greater than about 900 bp, e.g., greater than about 1000 bp, greater than about 1500 bp, greater than about 1800 bp, and greater than about 2100 bp. In the present application, the length of the heavy chain storage vector fragment may be substantially different from the length of the HC. For example, the length of the light chain storage vector fragment may be substantially distinguished from the length of the HC by means of PAGE.

In the present application, the heavy chain storage vector may be derived from any vector, such as, any vector that may be amplified and/or easy to store. In some cases, the vector used as the heavy chain storage vector may have properties like high copies, low molecular weight, etc. For example, the heavy chain storage vector may be a pUC vector. In the present application, the pUC vector may be a pUC19 vector (the schematic structural view of which may be as shown in FIG. 1) or be derived from the pUC19 vector. In the present application, the pUC vector may be or be derived from a pMD19-T vector.

In the present application, to construct the heavy chain storage vector, the vector which is or is derived from the pUC vector may be engineered/modified. For example, it is feasible to remove one or more endonuclease recognition sites from the vector (e.g., to remove one or more BsmBI recognition sites therefrom) by site-directed mutagenesis. In some cases, it is also feasible to add one or more endonuclease recognition sites into the vector (e.g., to add one or more BsmBI recognition sites at selected positions) by site-directed mutagenesis.

In an example, it is feasible to remove one or more of the existing BsmBI endonuclease recognition sites from the vector by site-directed mutagenesis, and then add one or more additional BsmBI recognition sites into another position of the vector to obtain the modified vector (e.g., a modified pUC vector).

In the present application, the heavy chain storage vector may include and only includes one BsmBI recognition site.

In the present application, the restriction endonuclease recognizing the R5 and R6 may include SfiI, BsmBI and/or Esp3I. In some cases, the restriction endonuclease recognizing the R5 and R6 is BsmBI and/or Esp3I.

In the present application, the 2) includes connecting the second polynucleotide to a vector fragment to form a connexon storage vector (e.g., in accordance with the instructions of TA clone product of Takara Inc.), and introducing the connexon storage vector into the second bacterium to obtain the connexon component bacteria. In the present application, the connexon storage vector may include the R3 and R4 sites.

In the present application, the connexon may have a length of greater than about 70 bp, e.g., about 72 bp, or about 90 bp. In the present application, the second polynucleotide may have a length of greater than about 80 bp, e.g., greater than about 90 bp, greater than about 100 bp, and greater than about 120 bp. In the present application, the vector fragment may have a length of greater than about 800 bp.

In the present application, the vector fragment for constructing the connexon storage vector may be derived from any vector, such as, any vector that may be amplified and/or easy to store. In some cases, the vector for constructing the connexon storage vector may have properties including high copies, low molecular weight, etc. For example, the vector fragment for constructing the connexon storage vector may be derived from a pUC vector. In the present application, the pUC vector may be a pUC19 vector (the schematic structural view of which may be as shown in FIG. 1) or be derived from the pUC19 vector. In the present application, the pUC vector may be or be derived from a pMD19-T vector.

In the present application, the pUC19 vector or the pMD19-T vector includes a vector that is derived therefrom but modified/engineered.

In the present application, the 4) may include digesting the light chain component plasmid with a restriction endonuclease recognizing the R1 and R2 so as to obtain the released LC. In the present application, the restriction endonuclease recognizing the R1 and R2 may include SfiI.

In the present application, the 4) may include digesting the heavy chain component plasmid with a restriction endonuclease recognizing the R5 and R6, so as to obtain the released HC. In the present application, the restriction endonuclease recognizing the R5 and R6 may include SfiI, BsmBI and/or Esp3I.

In some cases, in the present application, the 4) may include digesting the connexon storage vector with a restriction endonuclease recognizing the R3 and R4, so as to obtain the released connexon.

For example, it is feasible to directly digest the connexon storage vector with a restriction endonuclease recognizing the R3 and R4 (e.g., SfiI) to obtain the released connexon. In the present application, the connexon may have a length of about 72 bp or more, e.g., about 90 bp or more.

In some cases, in the present application, the 4) may include obtaining an amplification product including the connexon, the R3 and the R4 from the connexon storage vector; and digesting the amplification product with the restriction endonuclease recognizing the R3 and R4 so as to obtain the released connexon.

For example, it is feasible to obtain the amplification product including the connexon, the R3 and the R4 by means of PCR and other methods, wherein the amplification product may have a length of about 800 bp or more, e.g., about 900 bp or more, about 1000 bp or more, and about 1200 bp or more. In the present application, it is feasible to digest the amplification product with the restriction endonuclease recognizing the R3 and R4 (e.g., SfiI) to obtain the released connexon. In the present application, the connexon may have a length of about 72 bp or more, and about 90 bp or more. In the present application, the length of the amplification product may be substantially different from the length of the connexon. In this way, a single connexon may be obtained more easily and efficiently. For example, the length of the amplification product may be substantially distinguished from the length of the connexon by means of PAGE.

In the present application, the restriction endonuclease recognizing the R3 and R4 may include SfiI.

In the present application, the 5) may include digesting the display vector with a restriction endonuclease recognizing the R7 and R8 to release the display vector fragment. In the present application, the restriction endonuclease recognizing the R7 and R8 may include SfiI, BsmBI and/or Esp3I.

In the present application, the display vector may be derived from any suitable vector, such as, a pComb3x vector. The pComb3x vector may be modified to adapt to the purpose of the present application. For example, the pComb3x vector may include one SfiI recognition site located at the 5'-terminal and one SfiI recognition site located at the 3'-terminal. During the modification process, the SfiI recognition site at the 3'-terminal of the pComb3x vector may be removed by site-directed mutagenesis. In some cases, the site-directed mutagenesis cannot affect the intraframe expression of protein (e.g., antibody heavy chain fragments and/or antibody light chain fragments) in the vector. For example, the mutation may be non-sense mutation, e.g., mutations that only change the base sequence, but do not change the amino acid sequence.

In the present application, three different digested fragments can be obtained after the display vector is digested with the restriction endonuclease recognizing the R1, R2, R3, R4, R5 and R8. For example, the display vector may include 3 restrictive endonuclease recognition sites that can be recognized by SfiI. Three different digested fragments can be obtained when digesting the display vector with SfiI.

In the present application, the restriction endonuclease recognizing the R1, R2, R3, R4, R5 and R8 may include SfiI. In the present application, after digesting the display vector with the restriction endonuclease recognizing the R6 and R7, the display vector may be linearized.

In the present application, the restriction endonuclease recognizing the R6 and R7 may include BsmBI and/or Esp3I.

In the present application, four different digested fragments can be obtained after the display vector is digested with the restriction endonuclease recognizing the R1, R2, R3, R4, R5, R6, R7 and R8. For example, the display vector may include 3 restrictive endonuclease recognition sites that can be recognized by SfiI and 1 restrictive endonuclease recognition site that can be recognized by BsmBI and/or Esp3I. Four different digested fragments can be obtained when the display vector is digested with SfiI, BsmBI and/or Esp3I.

For example, it is feasible to utilize the restriction endonuclease R1 and R2 to obtain the released LC; and utilize the restriction endonuclease R5 and R6 to obtain the released HC;

In the present application, the restriction endonuclease recognizing the R1, R2, R3, R4, R5, R6, R7 and R8 may include SfiI, BsmBI and/or Esp3I.

In the present application, the vector (e.g., the display vector or storage vector) may include or encode one or more suitable markers (e.g., those for use in purification/recognition/screening), which may be, e.g., His tag, Flag Tag, fluorescein, selective antibiotic, and/or avidin, etc.

In the present application, the 2) may include detecting samples from the light chain component bacterial library, the connexon component bacterial library and/or the heavy chain component bacterial library to determine a library capacity and/or quality of the light chain component bacterial library, the connexon component bacterial library and/or the heavy chain component bacterial library.

In the present application, the light chain component bacterial library may include at least about $10^6$ (e.g., at least about $10^7$, at least about $10^8$, at least about $10^9$, at least about $10^{10}$, at least about $10^{11}$, and at least about $10^{12}$ or more) different clones.

In the present application, the heavy chain component bacterial library may include at least about $10^7$ (e.g., at least about $10^8$, at least about $10^9$, at least about $10^{10}$, at least about $10^{11}$, and at least about $10^{12}$ or more) different clones.

In the present application, the effective cloning proportion in the light chain component bacterial library may be at least about 70% (e.g., at least about 75%, at least about 80%, at least about 85%, at least about 90%, at least about 95%, and at least about 99%).

In the present application, the effective cloning proportion in the heavy chain component bacterial library may be at least about 70% (e.g., at least about 75%, at least about 80%, at least about 85%, at least about 90%, at least about 95%, and at least about 99%).

In the present application, the 2) includes calculating a capacity and/or quality of the display bacterial library based on the library capacity of the light chain component bacterial library and/or the heavy chain component bacterial library, the connexon component bacterium and/or mass.

In the present application, the display bacterial library may include at least about $10^{10}$ (e.g., at least about $10^{11}$, at least about $10^{12}$, at least about $10^{13}$, at least about $10^{14}$, at least about $10^{15}$, and at least about $10^{16}$ or more) different clones.

In the present application, the effective cloning proportion in the display bacterial library may be at least about 70% (e.g., at least about 75%, at least about 80%, at least about 85%, at least about 90%, at least about 95%, and at least about 99%).

In the present application, the bacterium in the display bacterial library may be subject to liquid culture. The culture time of liquid culture may be not greater than about 8 hours, e.g., not greater than about 4 hours, not greater than about 5 hours, not greater than about 6 hours or not greater than about 7 hours. In the present application, the operation for liquid culture is relatively easy and convenient. In some cases, the bacterium in the display bacterial library may be subject to dish culture with a small amount of bacterial solution, followed by picking colonies. The culture time of the dish culture may be about 12-18 hours, for example, it may be about 12 hours, 13 hours, 14 hours, 15 hours, 16 hours, 17 hours or 18 hours. In the present application, the dish culture may include selecting colonies (e.g., selecting monoclones) for sequencing. In the present application, the dish culture may reduce the number of dominant clones.

In the present application, the first polynucleotide and the third polynucleotide may be obtained from a sample material. In the present application, the sample material may include a sample material derived from peripheral blood lymphocyte sample. In the present application, the peripheral blood lymphocyte may be human peripheral blood lymphocyte. In the present application, the sample material may also be derived from any other tissues and/or cells, and is not limited to the peripheral blood lymphocyte sample.

In the present application, the sample material may include total RNA and/or mRNA derived from the sample.

In the present application, the 8) may include contacting the display bacterial library with a helper phage to prepare the phage library.

In another aspect, the present application provides a phage library produced by the method as described.

In the present application, the phage library may include at least about $10^{10}$ (e.g., at least about $10^{11}$, at least about $10^{12}$, at least about $10^{13}$, at least about $10^{14}$, at least about $10^{15}$, and at least about $10^{16}$ or more) different clones. In the present application, the phage library may display at least about $10^{10}$ (e.g., at least about $10^{11}$, at least about $10^{12}$, at least about $10^{13}$, at least about $10^{14}$, at least about $10^{15}$, and at least about $10^{16}$ or more) different antibodies or antibody fragments.

In another aspect, the present application provides a method for screening antibodies or antibody fragments, including using the phage library.

For example, the antibody fragment may be Fab. For example, the antibodies or antibody fragments may specifically bind to TNFα, IL-6, IL6R, IL17-FR, CD38, GMCSF and Siglec3.

Without being limited by any theory, the following examples are only for illustrating the fusion proteins, preparation methods, and use of the present application, and are not intended to limit the scope of the invention of the present application.

EXAMPLES

Example 1. Construction of Phage Surface Antibody (Fab) Display Library of Human PBMC 1.1 Obtainment of Total RNA/mRNA of Immune Materials Total RNA was extracted from human peripheral blood lymphocytes (PBMCs), and mRNA was further isolated from the total RNA (Takara Cat #Z652N/636592, see the product instructions for the specific test procedures).

1.2 Design of Synthesis Primer

Referring to the Phage Display (A Laboratory Mannual, ISBN 0-87969-546-3), primers for a human heavy chain variable region VH, a light chain KLC (a full-length Kappa light chain), and a light chain LLC (a full-length Lamda light chain). Of those, in the light chain, the 5'-terminal of the forward primer includes the nucleotide sequence of R1: GGCCCAGGCGGCC (SEQ ID NO: 1), the 5'-terminal of the reverse primer includes the nucleotide sequence of R2: GGCCACATAGGCC (SEQ ID NO: 2); in the heavy chain variable region, the 5'-terminal of the forward primer includes the nucleotide sequence of R5: GGCCCAACCGGCC (SEQ ID NO: 3), and the 5'-terminal of the reverse primer includes the nucleotide sequence of R6: CGTCTCCTCAGC (SEQ ID NO: 4). The primers were synthesized by Genewiz, Inc.

By taking the pComb3x vector as template, the forward and reverse primers were designed and amplified. Of those, the 5'-terminal of the forward primer includes the nucleotide sequence of R3: GGCCACATAGGCC (SEQ ID NO: 2), and the 5'-terminal of the reverse primer includes the nucleotide sequence of R4: GGCCCAACCGGCC (SEQ ID NO: 3).

For the particular primer sequences, please refer to Table 1-1 as below.

TABLE 1-1

Primer Sequences-1

| Primer Name | SEQ ID NO: |
| --- | --- |
| Forward primer of light chain KLC | 5-22 |
| Reverse primer of light chain KLC | 23 |
| Forward primer of light chain LLC | 24-48 |
| Reverse primer of light chain LLC | 49 |
| Forward primer of VH | 50-73 |
| Reverse primer of VH | 74-78 |
| Forward primer of connexon | 79 |
| Reverse primer of connexon | 80 |

1.3 Obtainment of First Polynucleotide and Third Polynucleotide

The gene library of component antibodies was amplified in two steps.

In the first step, by taking the mRNA obtained in Example 1.1 as a template, a cDNA was synthesized by reverse transcription of MMLV from Promega (according to the product instructions of Promega, Inc., in which the primer was Thermo Cat #N8080127, and the reverse transcriptase was Promega Cat #M1701).

In the second step, by taking the cDNA obtained in the first step as a template and using the primer obtained in Example 1.2, the KLC, LLC and VH gene libraries of component antibodies were amplified by PCR (Takara Cat #RR900A, according to the product instructions of the corporation). After purification for recovery by gel electrophoresis (operating by using the gel recovery kit from Axygen and in accordance with the disclosure in the *Molecular Cloning Experimental Guidelines*), the PCR products—KLC fragment (i.e., the first polynucleotide of the present application), the LLC fragment (the first polynucleotide of the present application) and the VH fragment (the third polynucleotide of the present application) were obtained respectively.

1.4 Construction of Storage Vector 1.4.1 Design of Primers

The primers were designed by reference to the procedures of Example 1.2.

The primers for obtaining the storage vectors were designed and synthesized. For the particular primer sequences, please refer to Table 1-2 as below.

TABLE 1-2

Primer Sequences-2

| Primer Name | SEQ ID NO: |
| --- | --- |
| Forward primer of R1-1kb-R2 | 81 |
| Reverse primer of R1-1kb-R2 | 82 |
| Forward primer of R5-1kb-R6 | 85 |
| Reverse primer of R5-1kb-R6 | 86 |

1.4.2 PCR Amplification

By taking 1kb IgG1 Fc in length (SEQ ID NO: 87) as a template, PCR was carried out by using the primers prepared in Example 1.4.1, the forward primer and reverse primer of R1-1kb-R2. After purification for recovery by gel electrophoresis (by using the gel recovery kit from Axygen), the PCR product—R1-1kb-R2 (SEQ ID NO: 88) was obtained.

By taking the pComb3x vector as a template, PCR was carried out by using the forward primer (SEQ ID NO: 83) and the reverse primer (SEQ ID NO: 84) of R3-connexon-R4. After purification for recovery by gel electrophoresis (by using the gel recovery kit from Axygen), the PCR product—R3-connexon-R4 (SEQ ID NO: 90) was obtained, thereby giving the second polynucleotide of the present application. Of those, the connexon may have a length of 72 bp, and the nucleotide sequence is as shown in SEQ ID NO:89.

By taking 1kb Fc of human IgG1 in length (SEQ ID NO: 87) as a template, PCR was carried out by using the primers prepared in Example 1.4.1, the forward primer and reverse primer of R5-1kb-R6. After purification for recovery by gel electrophoresis, a PCR product was obtained—R5-1kb-R6 (SEQ ID NO: 91).

1.4.3 Construction of Light Chain Storage Vector and Heavy Chain Storage Vector

Figure 3:
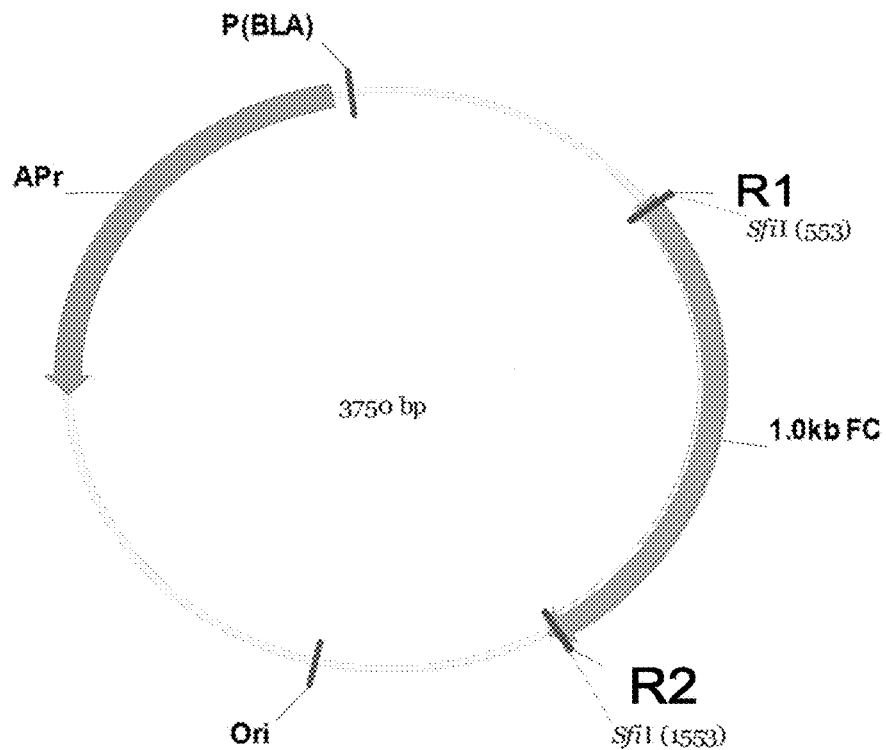
FIG. 3 shows a schematic diagram of the light chain storage vector of the present application.

By means of a TA cloning (a TA cloning kit, purchased from Takara Inc.) method, the R1-1kb-R2 fragment prepared in 1.4.2 was inserted into a pMD19-T vector to obtain the light chain storage vector DDB-R1-1kb-R2 for insertion into the full-length light chain gene library. The vector map is as shown in FIG. 3.

Figure 5:
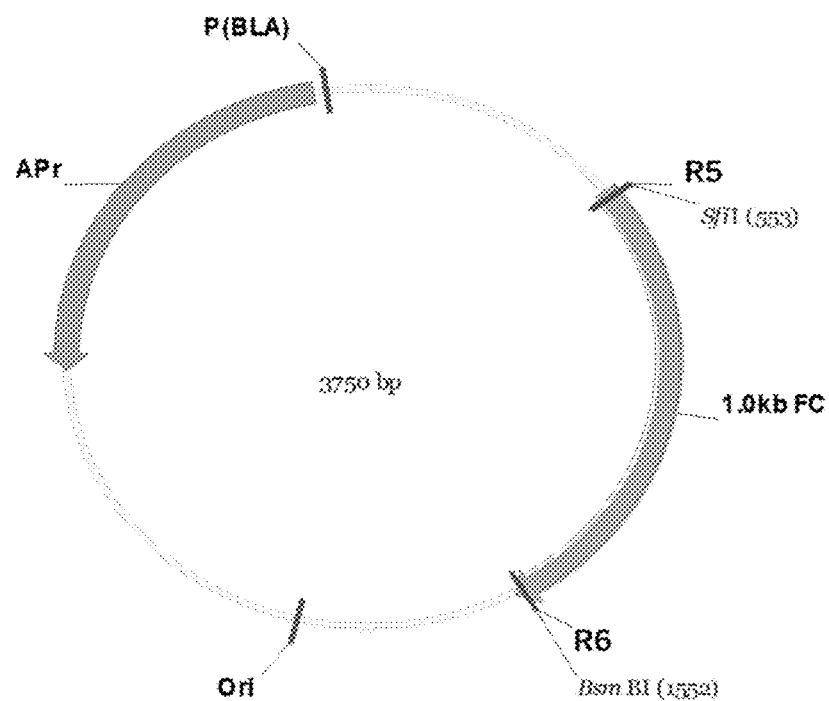
FIG. 5 shows a schematic diagram of the heavy chain storage vector of the present application.

By means of a TA cloning (a TA cloning kit, purchased from Takara Inc.) method, the R5-1kb-R6 fragment prepared in 1.4.2 was inserted into a pMD19-T vector to obtain the vector including the R5-1kb-R6 fragment. Next, by taking this vector as a template, the original BsmBI digestion site was removed from this vector by primer mutation to obtain the heavy chain storage vector DDB-R5-1kb-R6 for insertion into the VH gene library. The vector map is as shown in FIG. 5.

For the particular primer sequences, please refer to Table 1-3 as below.

TABLE 1-3

Primer Sequences-3

| Primer Name | SEQ ID NO: |
| --- | --- |
| Forward primer of vector mutation | 92 |
| Reverse primer of vector mutation | 93 |

Figure 4:
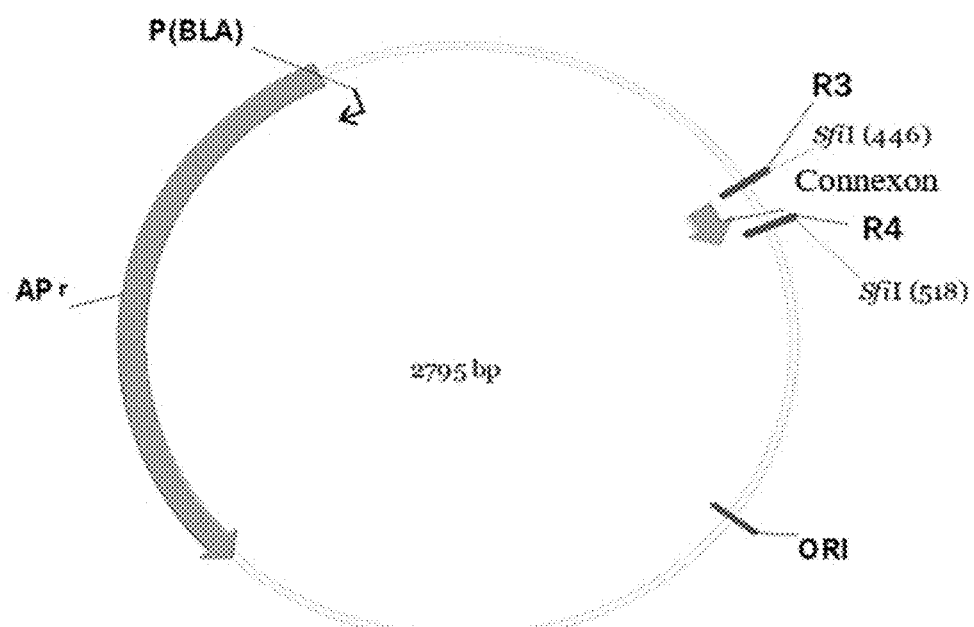
FIG. 4 shows a schematic diagram of the connexon storage vector of the present application.

1.4.4 Construction of Connexon Storage Vector and Obtainment of Connexon Component Bacteria By means of a TA cloning (a TA cloning kit, purchased from Takara Inc.) method, the R3-connexon-R4 prepared in Example 1.4.2 was inserted into a pMD19-T vector to obtain the connexon storage vector DDB-R3-connexon-R4. The vector map is as shown in FIG. 4. The connexon storage vector can be used to transform TG1 competence bacteria (Lucigen, Inc.), followed by dish culture at 37° C. overnight. The colonies were sequenced, and then collected to obtain the connexon component bacteria. The connexon component bacteria can be cryopreserved for use 1.5 Obtainment of Component Bacterial Library 1.5.1 Obtainment of Light Chain Component Bacterial Library The first polynucleotide (including KLC and LLC) prepared in Example 1.3 was digested with the restriction endonuclease R1 and R2 to obtain the target light chain fragment (about 0.65 kb).

The light chain storage vector DDB-R1-1kb-R2 prepared in Example 1.4 was digested with the restriction endonuclease R1 and R2. The light chain storage vector fragment (about 2.7 kb) was obtained.

The obtained target light chain fragment and the light chain storage vector fragment were mixed and connected with a ligase T4 DNA ligase (purchased from NEB, Thermo) to obtain the light chain storage connection product. Then, the light chain storage connection product was used to transform TG1 competence bacteria (Lucigen, Cat #60502-2, operated in accordance with the manufacturer's instructions) by culturing in an ampicillin-resistant dish (Thermo, Cat #240845) at 37° C. overnight. The colonies were picked for sequencing, and then all the colonies were collected to obtain the light chain component bacterial library. The light chain component bacterial library can be detected for its quality and/or the light chain component bacterial library can be cryopreserved for use 1.5.2 Obtainment of Heavy Chain Component Bacterial Library The third polynucleotide prepared in Example 1.3 was digested with the restriction endonuclease R5 and R6 to obtain the target heavy chain variable region fragment (about 0.35 kb).

The heavy chain storage vector DDB-R5-1kb-R6 prepared in Example 1.4 was digested with the restriction endonuclease R5 and R6. The heavy chain storage vector fragment (about 2.7 kb) was obtained.

The obtained target heavy chain variable region fragment and the heavy chain storage vector fragment were mixed and connected with a ligase T4 DNA ligase (purchased from NEB, Thermo) to obtain the heavy chain storage connection product. Then, the heavy chain storage connection product was used to transform TG1 competence bacteria (Lucigen, Cat #60502-2, operated in accordance with the manufacturer's instructions) by culturing in an ampicillin-resistant dish (Thermo, Cat #240845) at 37° C. overnight. The colonies were picked for sequencing, and all the colonies were collected to obtain the heavy chain component bacterial library. The heavy chain component bacterial library can be detected for its quality and/or the heavy chain component bacterial library can be cryopreserved for use.

1.6 Obtainment of Light Chain Component Plasmid, Heavy Chain Component Plasmid and Connexon Fragment The plasmids in the light chain component bacterial library prepared in Example 1.5.1 and the heavy chain component bacterial library prepared in Example 1.5.2 were extracted with a plasmid extraction kit (purchased from Axygen) to obtain the light component plasmid and the heavy component plasmid, respectively.

The light chain component plasmid prepared in Example 1.5.1 was digested with the restriction endonuclease R1 and R2, and purified and recovered by gel electrophoresis to obtain the light chain insert fragment LC.

The heavy chain component plasmid prepared in Example 1.5.2 was digested with the restriction endonuclease R5 and R6, and purified and recovered by gel electrophoresis to obtain the heavy chain insert fragment HC.

The plasmids in the connexon component bacteria prepared in Example 1.4.4 were extracted with a plasmid extract kit (purchased from Axygen) to obtain the connexon component plasmid. By taking the connexon component plasmid or the connexon storage vector in Example 1.4.4 as a template, a 0.8 kb connexon-containing fragment was amplified with the forward primer (SEQ ID NO: 79) and the reverse primer (SEQ ID NO: 80) of the connexon, and then the PCR product of the 0.8 kb was digested with the restriction endonuclease R3 and R4, purified for recovery by gel electrophoresis (with small fragment gel recovery, purchased from LifeFeng Biotech, Cat #DK402) to obtain a 72pb connexon fragment.

1.7 Obtainment of Display Vector

Figure 6:
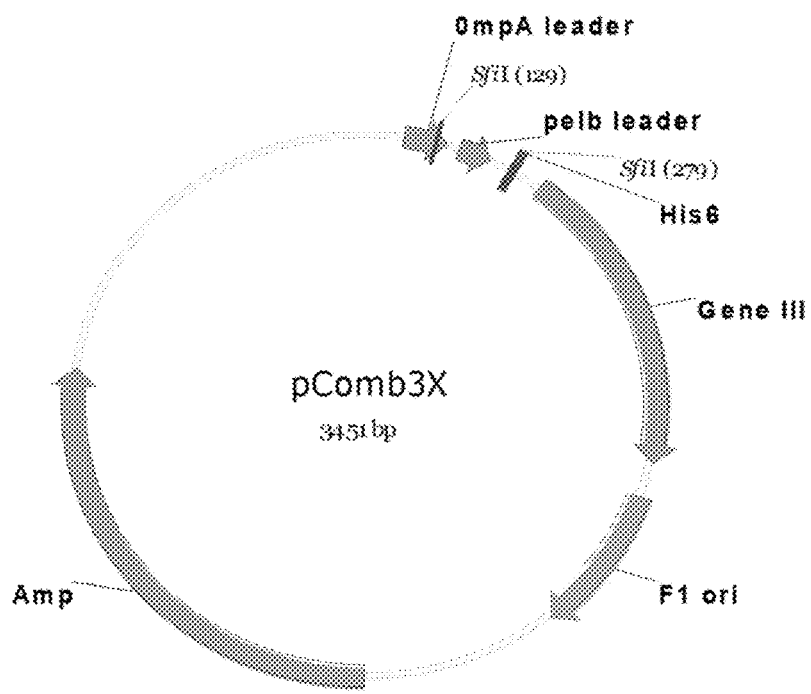
FIG. 6 shows a schematic diagram of pCom3x vector.
Figure 7:
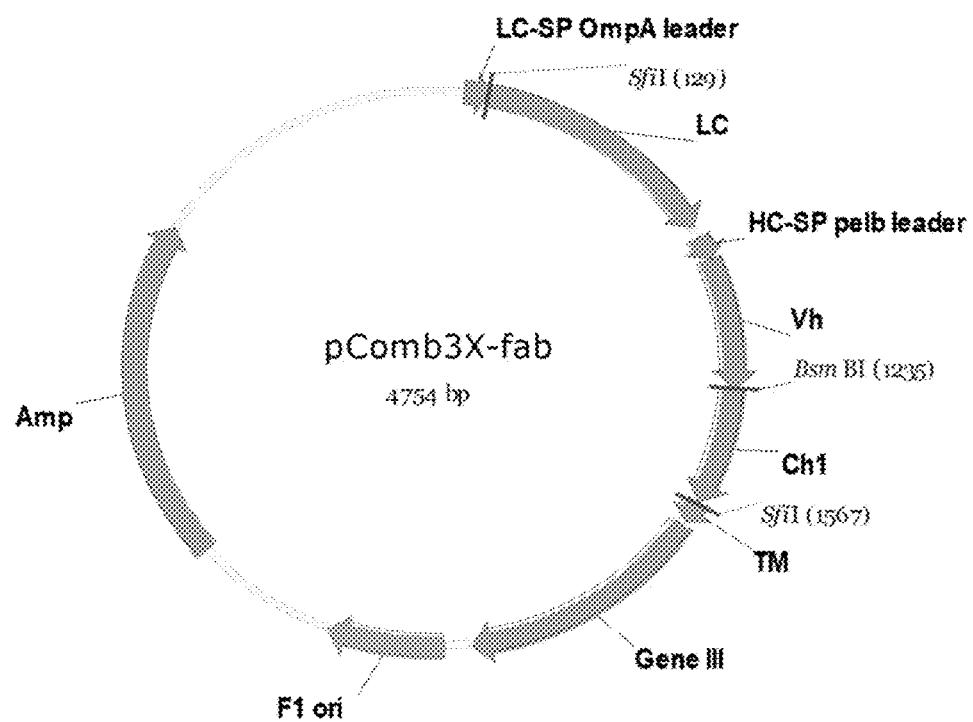
FIG. 7 shows a schematic diagram of the display vector of the present application.

The pComb3x vector was obtained by purchase. The vector map is as shown in FIG. 6, wherein the map of the modified pComb3x-fab vector for antibody Fab display is as shown in FIG. 7.

The SfiI digestion site at the 3' terminal of the Fab gene in the pComb3x-fab vector was removed by non-sense mutation.

Figure 8:
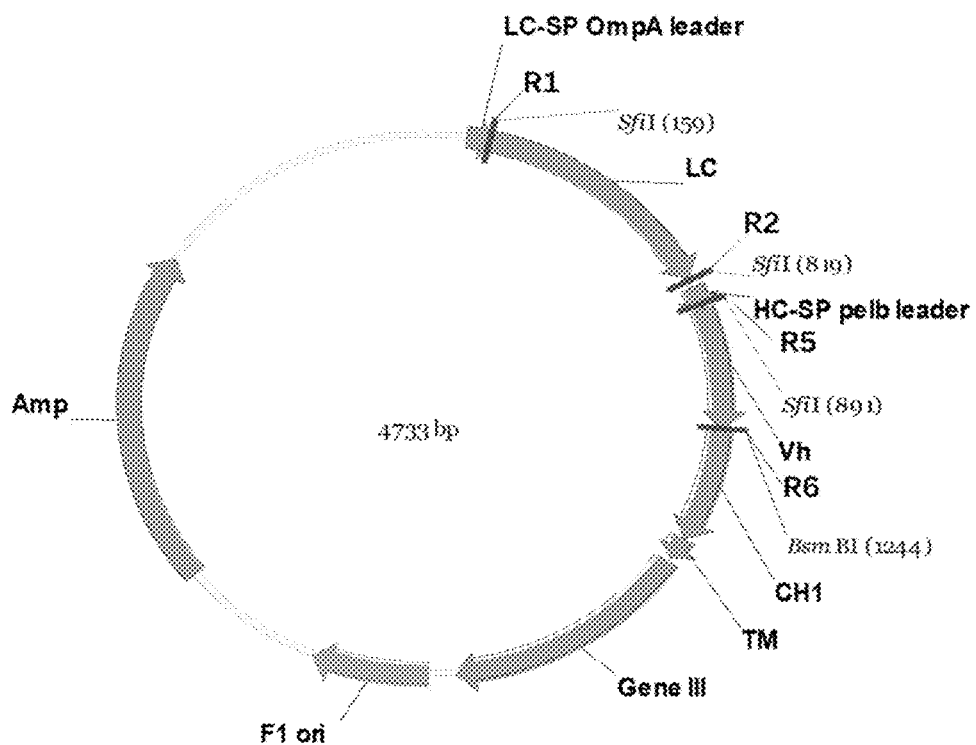
FIG. 8 shows a schematic diagram of a plasmid including the connection product for display of the present application.

Then, the digestion site of the restriction endonuclease R2 was added into the downstream of the stop codon of the light chain in the non-sense mutant vector, the digestion site of the restriction endonuclease R5 was introduced to the terminal of the heavy chain variable region signal peptide by non-sense mutation, to obtain the modified display vector DDB-R1R2R5R6. The map thereof is as shown in FIG. 8.

1.8 Preparation of Display Bacterial Library

The display vector DDB-R1R2R5R6 prepared in Example 1.7 was digested with the restriction endonuclease R7 and the restriction endonuclease R8 to obtain a 3.6 kb display vector fragment.

The light chain insert fragment LC (0.65 kb), the heavy chain insert fragment HC (0.35 kb), the connexon fragment (72 bp), and the display vector fragment (3.6 kb) obtained in Example 1.6 were mixed in a molecular ratio of 1:1:1:1, and connected with a T4 DNA ligase at 20° C. for 20 hours or more to obtain the connection product for display.

The connection product was purified with PCR-Clean-up, transformed into TG1 competence bacteria (Lucigen, Cat #60502-2, operated in accordance with the manufacturer's instructions), cultured under shaking in antibiotic-free 2YT culture medium at 37° C. at 250 rpm for 60 minutes, and cultured in an ampicillin-resistant dish (Thermo, Cat

240845) at 37° C. for growth overnight. The colonies were picked for sequencing. All the colonies grown on the dish were collected to obtain the display bacterial library. The display bacterial library can be stored for use.

1.9 Preparation of Antibody Phage Display Library

An appropriate amount of bacterial solution was taken from the display bacterial library prepared in Example 1.8, and cultured in 2YT culture medium (containing 100 μG/ml of ampicillin and 2% glucose) at 37° C. until $OD_{600}$ reaches 0.5. Then, M13KO7 auxiliary phage (purchased from NEB, Cat #N0315S, with MOI of about 10-20) was added into the bacteria solution, mixed well, and stood at 37° C. for 30 minutes. Next, the mixture was shaken at 37° C., 250 rpm for 30 minutes, and centrifuged. The supernatant containing M13KO7 auxiliary phage was discarded. The cells were re-suspended in 4× original volume of the bacterial solution (containing ampicillin and kanamycin), and shaken at 30° C., 250 rpm overnight. On the next day, the phage was collected by PEG precipitation, titrated for the phage concentration, and subpacked for storage to obtain the display antibody phage library.

Example 2 Quality Analysis of Component Bacteria Library

The component bacterial library prepared in Example 1.5 was analyzed for its quality. The results are shown in Table 2.

TABLE 2

Quality of Component Bacteria Library

| Component Library | Library Capacity | Number of Clones in Samples | Available Sequencing Reports | Correct Frame Readings | Repeated Sequences | Effective Cloning Proportion |
|---|---|---|---|---|---|---|
| Heavy chain component bacterial library | $10^8$ | 40 | 32 | 31 | 0 | 97% |
| Light chain component bacterial library (KLC) | $10^7$ | 20 | 16 | 13 | 0 | 81% |
| Light chain component bacterial library (LLC) | $10^7$ | 20 | 18 | 18 | 0 | 100% |

When the display bacterial library is constructed, the ratio of the light chain component bacterial library (KLC) to the light chain component bacterial library (LLC) is 2:1. According the quality results as above, it can be estimated that the effective cloning proportion of the display bacterial library will reach 84% or more. The library capacity obtained by random combination of the light chain component bacterial library and the heavy chain component bacterial library can theoretically reach $10^{15}$.

Example 3. Quality Analysis of Display Bacterial Library

197 μg of the isolated and purified connection product for display obtained in Example 1.8 was used to transform 398 TG1 competence bacteria (Lucigen, Cat #60502-2, operated in accordance with the manufacturer's instructions). They were cultured under shaking in antibiotic-free 2YT culture medium at 37° C. at 250 rpm for 60 minutes, and then cultured in 197 ampicillin-resistant dishes (Thermo, Cat #240845) at 37° C. overnight. All the colonies were harvested, and subpacked for storage (to obtain the display bacterial library prepared in Example 1.8). The library capacity of the display bacterial library is $10^{11}$, and the background cloning proportion is 2%.

The display bacterial library was analyzed for its quality, and the results are shown as Table 3:

TABLE 3

Quality of Display Bacterial Library

| Sequencing Batch | Samples of Sequencing Clones | Available Sequencing Reports | Correct Frame Readings | Repeated Sequences | Effective Clones | Effective Cloning Proportion |
|---|---|---|---|---|---|---|
| First Batch | 100 | 79 | 65 | 1 | 64 | 81% |
| Second Batch | 100 | 79 | 67 | 0 | 67 | 85% |

The useful sequencing results (158 in total in two batches) in Table 3 were analyzed, of which 131 clones have correct reading frames (including those including both correct heavy chain variable regions and correct light chain). It can be seen that the effective cloning proportion of the display bacterial library reaches 83%, which is consistent with the estimated results in Example 2.

Example 4. Construction of Phage Surface Antibody (Fab) Display Library of Human PBMC 4.1 Extraction of Total RNA of Immune Materials Total RNA was extracted from the peripheral blood lymphocyte (purchased from MT Bio, Cat #PB100C) (with an RNA mini kit from Qiagen, Cat #74101, see the instructions of kit for the specific test procedures).

4.2 Design of Synthesis Primer

Referring to the Phage Display (A Laboratory Mannual, ISBN 0-87969-546-3), primers for human heavy chain variable region VH, light chain KLC (a full-length Kappa light chain), light chain LLC (a full-length Lamda light chain) are designed. Of those, in the light chain, the 5'-terminal of the forward primer includes the nucleotide sequence of R1: GGCCCAGGCGGCC (SEQ ID NO: 1), the 5'-terminal of the reverse primer includes the nucleotide sequence of R2: GGCCACATAGGCC (SEQ ID NO: 2); in the heavy chain variable region, the 5'-terminal of the forward primer includes the nucleotide sequence of R5: GGCC-CAACCGGCC (SEQ ID NO: 3), the 5'-terminal of the reverse primer includes the nucleotide sequence of R6: CGTCTCCTCAGC (SEQ ID NO: 4). The primers were synthesized by Genewiz, Inc.

By taking the pComb3x vector as a template, the forward and reverse primers of the connexon were designed and amplified. Of those, the 5'-terminal of the forward primer includes the nucleotide sequence of R3: GGCCACAT-AGGCC (SEQ ID NO. 2), the 5'-terminal of the reverse primer includes the nucleotide sequence of R4: GGCC-CAACCGGCC (SEQ ID NO: 3).

For the particular primer sequences, please refer to Table 4-1 as below.

TABLE 4-1

Primer Sequences-1

| Primer Name | SEQ ID NO: |
|---|---|
| Forward primer of light chain KLC | 5-22 |
| Reverse primer of light chain KLC | 23 |
| Forward primer of light chain LLC | 24-48 |
| Reverse primer of light chain LLC | 49 |
| Forward primer of VH | 50-73 |
| Reverse primer of VH | 74-78 |
| Forward primer of 90bp connexon | 96-97 |
| Reverse primer of 90bp connexon | 98 |

4.3 Obtainment of First Polynucleotide and Third Polynucleotide

The gene library of component antibodies was amplified in two steps.

In the first step, by taking the total RNA obtained in Example 4.1 as a template, a cDNA was synthesized by reverse transcription of MMLV from Promega (according to the instructions of Promega, Inc., in which the primer was Thermo Cat #N8080127, and the reverse transcriptase was Promega Cat #M1701).

In the second step, by taking the cDNA obtained in the first step as a template and using the primer obtained in Example 4.2, the KLC, LLC and VH gene libraries of component antibodies were amplified by PCR (Takara Cat #RR900A, according to the product instructions of the corporation). After purification for recovery by gel electrophoresis (operating by using the gel recovery kit from Axygen and in accordance with the disclosure of the *Molecular Cloning Experimental Guidelines*), the PCR products—KLC fragment (i.e., the first polynucleotide of the present application), LLC fragment (the first polynucleotide of the present application) and VH fragment (the third polynucleotide of the present application) were obtained respectively.

4.4 Construction of Storage Vector 4.4.1 Design of Primers

A primer for obtaining a storage vector was designed. For the particular primer sequences, please refer to Table 4-2 as below.

TABLE 4-2

Primer Sequences-2

| Primer Name | SEQ ID NO: |
|---|---|
| Forward primer of R1-1kb-R2 | 81 |
| Reverse primer of R1-1kb-R2 | 82 |

TABLE 4-2-continued

Primer Sequences-2

| Primer Name | SEQ ID NO: |
|---|---|
| Forward primer of R5-1kb-R6 | 85 |
| Reverse primer of R5-1kb-R6 | 86 |

4.4.2 PCR Amplification

By taking 1kb Fc of human IgG1 in length (SEQ ID NO. 87) as a template, PCR was carried out by the primers prepared in Example 4.4.1, the forward primer and reverse primer of R1-1kb-R2. After purification for recovery by gel electrophoresis (by using the gel recovery kit from Axygen), a PCR product was obtained—R1-1kb-R2 (SEQ ID NO. 88).

By taking the pComb3x vector as a template, PCR was carried out by the forward primer of R3-connexon-R4 (SEQ ID NO. 83) and the reverse primer (SEQ ID NO. 84) of R3-connexon-R4. After purification for recovery by gel electrophoresis (by using the gel recovery kit from Axygen), a PCR product was obtained—R3-connexon-R4 (SEQ ID NO. 95), thereby obtaining the second polynucleotide of the present application. Of those, the connexon can have a length of 90 bp, and the nucleotide sequence thereof is as shown in SEQ ID NO.89.

By taking 1kb Fc of human IgG1 in length (SEQ ID NO. 87) as a template, PCR was carried out with the primers prepared in Example 4.4.1, the forward primer and the reverse primer of R5-1kb-R6. After purification for recovery by gel electrophoresis, a PCR product was obtained—R5-1kb-R6 (SEQ ID NO. 91).

4.4.3 Construction of Light Chain Storage Vector and Heavy Chain Storage Vector

By means of a TA cloning (a TA cloning kit, purchased from Takara Inc.) method, the R1-1kb-R2 fragment prepared in 4.4.2 was inserted into a pMD19-T vector to obtain the light chain storage vector DDB-R1-1kb-R2 for insertion into the full-length light chain gene library. The vector map is as shown in FIG. 3.

By means of a TA cloning (a TA cloning kit, purchased from Takara Inc.) method, the R5-1kb-R6 fragment prepared in 4.4.2 was inserted into a pMD19-T vector to obtain a vector including the R5-1kb-R6 fragment. Then, by taking this vector as a template, the original BsmBI digestion site was removed from the vector by primer mutation to obtain the heavy chain storage vector DDB-R5-1kb-R6 for insertion into the VH gene library. The vector map is as shown in FIG. 5.

For the particular primer sequences, please refer to Table 4-3 as below.

TABLE 4-3

Primer Sequences-3

| Primer Name | SEQ ID NO: |
|---|---|
| Forward primer of vector mutation | 92 |
| Reverse primer of vector mutation | 93 |

4.4.4 Construction of Connexon Storage Vector and Obtainment of Connexon Component Bacteria By means of a TA cloning (a TA cloning kit, purchased from Takara Inc.) method, the R3-connexon-R4 prepared in Example 4.4.2 was inserted into a pMD19-T vector to obtain the connexon storage vector DDB-R3-connexon-R4. The vector map is as shown in FIG. 4. The connexon storage vector can be used to transform TG1 competence bacteria (Lucigen, Inc.), followed by dish culture at 37° C. overnight. The colonies were sequenced, and then collected to obtain the connexon component bacteria. The connexon component bacteria can be cryopreserved for use 4.5 Obtainment of Component Bacterial Library 4.5.1 Obtainment of Light Chain Component Bacterial Library The first polynucleotide (including KLC and LLC) prepared in Example 4.3 was digested with the restriction endonuclease R1 and R2 to obtain a target light chain fragment (about 0.65 kb).

The light chain storage vector DDB-R1-1kb-R2 prepared in Example 4.4 was digested with the restriction endonuclease R1 and R2. The light chain storage vector fragment (about 2.7 kb) was obtained.

The obtained target light chain fragment and light chain storage vector fragment were mixed and connected with a ligase T4 DNA ligase (purchased from NEB, Thermo) to obtain the light chain storage connection product, and then the light chain storage connection product was used to transform TG1 competence bacteria (Lucigen, Cat #60502-2, operated in accordance with the manufacturer's instructions). The mixture was cultured under shaking in antibiotic-free 2YT culture medium at 37° C., 250 rpm for 60 minutes, and then cultured in an ampicillin-resistant dish (Thermo, Cat #240845) at 37° C. overnight. The colonies were picked for sequencing, and then all the colonies were collected to obtain the light chain component bacterial library. The light chain component bacterial library can be detected for its quality and/or the light chain component bacterial library can be cryopreserved for use 4.5.2 Obtainment of Heavy Chain Component Bacterial Library The third polynucleotide prepared in Example 4.3 was digested with the restriction endonuclease R5 and R6 to obtain a target heavy chain variable region fragment (about 0.35 kb).

The heavy chain storage vector DDB-R5-1kb-R6 prepared in Example 4.4 was digested with the restriction endonuclease R5 and R6. The heavy chain storage vector fragment (about 2.7 kb) was obtained.

The obtained target heavy chain variable region fragment and heavy chain storage vector fragment were mixed and connected with a ligase T4 DNA ligase (purchased from NEB, Thermo) to obtain the heavy chain storage connection product, and then the heavy chain storage connection product was used to transform TG1 competence bacteria (Lucigen, Cat #60502-2, operated in accordance with the manufacturer's instructions). The mixture was cultured under shaking in antibiotic-free 2YT culture medium at 37° C., 250 rpm for 60 minutes, and then cultured in an ampicillin-resistant dish (Thermo, Cat #240845) at 37° C. overnight. The colonies were picked for sequencing, and all the colonies were collected to obtain the heavy chain component bacterial library. The heavy chain component bacterial library can be detected for its quality and/or the heavy chain component bacterial library can be cryopreserved for use.

4.6 Obtainment of Light Chain Component Plasmid, Heavy Chain Component Plasmid and Connexon Fragment The plasmids in the light chain component bacterial library prepared in Example 4.5.1 and the heavy chain component bacterial library prepared in Example 4.5.2 were extracted with a plasmid extraction kit (purchased from Axygen) to obtain the light component plasmid and the heavy component plasmid, respectively.

The light chain component plasmid prepared in Example 4.5.1 was digested with the restriction endonuclease R1 and R2, and purified and recovered by gel electrophoresis to obtain the light chain insert fragment LC.

The heavy chain component plasmid prepared in Example 4.5.2 was digested with the restriction endonuclease R5 and R6, and purified and recovered by gel electrophoresis to obtain the heavy chain insert fragment HC.

The plasmids in the connexon component bacteria prepared in Example 4.4.4 were extracted with a plasmid extract kit (purchased from Axygen) to obtain the connexon component plasmid. By taking the connexon component plasmid or the connexon storage vector in Example 4.4.4 as a template, a 0.8 kb fragment including the connexon was amplified with the forward primer (SEQ ID NO.96 or SEQ ID NO.97) and the reverse primer (SEQ ID NO.98) of the connexon. Then, the 0.8 kb PCR product was digested with the restriction endonuclease R3 and R4. After purification for recovery by gel electrophoresis (with a small fragment gel recovery kit, purchased from LifeFeng Biotech, Cat #DK402), a 90pb connexon fragment was obtained.

4.7 Obtainment of Display Vector

The pComb3x vector was obtained by purchase. The vector map is as shown in FIG. 6, wherein the map of the modified pComb3x-fab vector for antibody Fab display is as shown in FIG. 7.

The SfiI digestion site at the 3' terminal of the Fab gene in the pComb3x-fab vector was removed by non-sense mutation.

Then, the digestion site of the restriction endonuclease R2 was added into the downstream of the stop codon of the light chain in the vector after non-sense mutation, the digestion site of the restriction endonuclease R5 was introduced to the terminal of the heavy chain variable region signal peptide by non-sense mutation, to obtain the modified display vector DDB-R1R2R5R6. The map thereof is as shown in FIG. 8.

4.8 Preparation of Display Bacterial Library

The display vector DDB-R1R2R5R6 prepared in Example 4.7 was digested with the restriction endonuclease R7 and the restriction endonuclease R8 to obtain a 3.6 kb display vector fragment.

The light chain insert fragment LC (0.65 kb), the heavy chain insert fragment HC (0.35 kb), the connexon fragment (90 bp), and the display vector fragment (3.6 kb) obtained in Example 4.6 were mixed in a molecular ratio of 1:1:1:1, and connected with a T4 DNA ligase at 20° C. for 20 hours or more to obtain the connection product for display.

The connection product was purified with PCR-Clean-up, and transformed into TG1 competence bacteria (purchased from Lucigen, Cat #60502-2). The mixture was cultured under shaking in antibiotic-free 2YT culture medium at 37° C., 250 rpm for 60 minutes, and then expanded at a ratio of 1:20 into ampicillin-containing 2YT culture medium at 37° C., 250 rpm for 4.5 hours. The bacteria were collected by centrifuge for cryopreservation, that is, the display bacterial library. Before expanding the culture with ampicillin, a small amount of bacterial solution was taken to culture in a dish at 37° C. overnight. The colonies were picked for sequencing. The display bacterial library can be stored for use.

4.9 Preparation of Display Antibody Phage Library

An appropriate amount of bacterial solution was taken from the display bacterial library prepared in Example 4.8, and cultured in 2YT culture medium (containing 100 μG/ml of ampicillin and 2% glucose) at 37° C. until $OD_{600}$ reaches 0.5. Then, M13KO7 auxiliary phage (purchased from NEB, Cat #N0315S, with MOI of about 10-20) was added into the bacteria solution, mixed well, and stood at 37° C. for 30 minutes. Next, the mixture was shaken at 37° C., 250 rpm for 30 minutes, and centrifuged. The supernatant containing M13KO7 auxiliary phage was discarded. The cells were re-suspended in 4× original volume of the bacterial solution (containing ampicillin and kanamycin), and shaken at 30° C., 250 rpm overnight. On the next day, the phage was collected by PEG precipitation, titrated for the phage concentration, and subpacked for storage to obtain the display antibody phage library.

Example 5 Quality Analysis of Component Bacteria Library

The component bacterial library prepared in Example 4.5 was analyzed for its quality. The results are as shown in Table 5.

TABLE 5

Quality of Component Bacteria Library

| | Library Capacity | Number of Clones in Samples | Available Sequencing Reports | Correct Frame Readings | Repeated Sequences | Effective Cloning Proportion |
|---|---|---|---|---|---|---|
| Heavy chain component bacterial library | $10^9$ | 40 | 23 | 22 | 0 | 96% |
| Light chain component bacterial library (KLC) | $10^9$ | 20 | 11 | 10 | 0 | 91% |
| Light chain component bacterial library (LLC) | $10^9$ | 20 | 17 | 13 | 0 | 76% |

When the display bacterial library is constructed, the ratio of the light chain component bacterial library (KLC) to the light chain component bacterial library (LLC) is 2:1. According to the above quality results, it can be estimated that the effective cloning proportion of the display bacterial library will reach 82%. The library capacity obtained by random combination of the light chain component bacterial library and the heavy chain component bacterial library can theoretically reach $10^{18}$.

Example 6. Quality Analysis of Display Bacterial Library

16 μg of the isolated and purified connection product for display obtained in Example 4.8 was used to transform 25 TG1 competence bacteria. After amplifying culture, the bacteria were collected by centrifuge to harvest $2.4 \times 10^{12}$ bacteria in total, which were subpacked for storage (to obtain the display bacterial library prepared in Example 4.8). The library capacity of the display bacterial library is $4 \times 10^{10}$, the background cloning proportion is 3%, and the conversion efficiency per μg of connection product reaches $2.5 \times 10^9$.

The quality of the display bacterial library was analyzed by two methods:

The first method: 90 colonies were randomly selected for sequencing. The results show that 56 colonies had correct reading frames and no repeated sequences. The cloning proportion of correct reading frames was 62.2%.

The second method: A plate was coated with anti-human Fab antibody, and the Fab expression of the above 90 clones was detected by ELISA. The results show that the readings of the two negative controls were 0.07 and 0.082, respectively. There were 71 clones in total with readings being higher than 0.1, which were identified as Fab expression. The positive proportion is 79%.

34 clones with sequence errors were analyzed, wherein 18 had Fab expression, accounting for 20% of the 90 clones. The clones with correct sequencing and those with expression but wrong sequencing was added (56+18), and the effective clone proportion reached 82.2% (74/90), which was consistent with the estimated results in Example 5.

Example 7 Quality Analysis of Display Antibody Phage Library

The display antibody phage library in Example 4.9 was precipitated with PEG. After precipitation by centrifugation, the cells were re-suspended in 280 ml PBS. 60 ml glycerin was added. The mixture was mixed well, and sub-packed for cryopreservation. The cryopreserved display antibody phage library was analyzed for the phage library titer. The results show that the titer of the phage library is $2 \times 10^{13}$/ml, the total amount of phages of the phage library is up to $6.8 \times 10^{15}$, and 100 μl includes 50 times the library capacity of phages.

To analyze whether antigen-specific antibodies can be screened from the constructed phage library, three secretory cytokines (IL6, IL17A/F, GMCSF) and three cell membrane proteins (IL6R, EGFR, Siglec3) were selected, and each antigen was screened with 100 μL of the phage library.

The antigen-specific Fab was screened by a liquid phase screening method using adsorption with biotinylated antigen-bonded avidin labeled magnetic beads. The above-mentioned six types of biotin-labelled antigens were purchased from AcroBiosystems (Item Numbers are sequentially Cat #IL6-H8218, ILF-H82W1, GMF-H8214, CD6-H82E8, EGR-H82E3 and CD3-H82E7), and the avidin-labelled magnetic beads were purchased from Thermo (Cat #11206D). The antigen concentrations of three rounds of liquid phase screening were 5 μg/ml, 3 μg/ml and 1 μg/ml, respectively. The phages collected by elution in the first round of screening were amplified for use in the second round of screening. The phages collected by elution in the second round of screening were directly used for the third round of screening without amplification.

The phages collected by elution in the third round of screening infected TG1 bacteria, and cultured in an ampicillin-coated dish at 37° C. overnight. On the next day, 96 monoclones were picked from each antigen-specific dish for culture and amplification (the culture medium in the dish included 2YT, 100 μg/ml of ampicillin, and 0.2% glucose) until $OD_{600}$ reached 0.6, and then IPTG was added (to a final concentration of 1 mM) for induction overnight. On Day 3, the antigen-specific Fab in the culture medium was analyzed by ELISA. The results are shown in Table 6.

TABLE 6

Proportion of Positive Clones Against Various Antigens

| Antigen | Maximum ELISA Reading | Minimum ELISA Reading | Number of Positive Clones | Proportion of Positive Clones |
| --- | --- | --- | --- | --- |
| IL6 | 1.029 | 0.147 | 54 | 56% |
| IL6R | 0.735 | 0.122 | 42 | 44% |
| IL17A/F | 1.395 | 0.133 | 49 | 51% |
| GMCSF | 0.925 | 0.066 | 84 | 87% |
| EGFR | 0.729 | 0.149 | 24 | 25% |
| Siglec3 | 0.981 | 0.114 | 76 | 79% |

In Table 6, the clones whose ELISA reading is greater than twice the minimum ELISA reading are counted as positive clones.

The results in Table 6 indicate that it is feasible to screen and obtain Fabs specific to IL-6, IL6R, IL17-FR, GMCSF, EGFR and Siglec3 from the phage antibody library, and the proportion of positive clones can reach about 25-87%.

From each group of antigen-specific positive clones, clones with top 12 ELISA reading were selected for sequencing analysis to align the amino acid sequences of 12 clones of each group. The results are shown in Table 7. The results in Table 7 indicate that each group has a plurality of unique amino acid sequences.

TABLE 7

Number of Monoclonal Fabs with Unique Amino Acid Sequences Against Various Antigens

| Antigen | IL-6 | IL6R | IL17A/F | GMCSF | EGFR | Siglec3 |
| --- | --- | --- | --- | --- | --- | --- |
| Number of Unique Fabs | 8 | 8 | 7 | 4 | 4 | 5 |

The aforesaid detailed description is provided in an illustrative and exemplary manner, and is not intended to limit the scope of the appended claims. Various modifications of embodiments currently listed in the present application are apparent for persons skilled in the art, and encompassed within the scope of the appended claims and their equivalences.

The invention claimed is:
1. A method for producing a phage library displaying an antibody or an antibody fragment, comprising:
   1) providing a first polynucleotide, a second polynucleotide and a third polynucleotide, said first polynucleotide contains a LC, said second polynucleotide contains a connexon, and said third polynucleotide contains a HC, wherein said LC comprises a nucleic acid sequence encoding a light chain or a light chain fragment of the antibody or the antibody fragment, and said HC comprises a nucleic acid sequence encoding a heavy chain or a heavy chain fragment of the antibody or the antibody fragment;
   2) introducing said first polynucleotide into a first bacterium to obtain a light chain component bacterial library, introducing said second polynucleotide into a second bacterium to obtain a connexon component bacterial library, and introducing said third polynucleotide into a third bacterium to obtain a heavy chain component bacterial library;
   3) obtaining a light chain component plasmid comprising said LC from said light chain component bacterial library, obtaining a connexon component plasmid comprising said connexon from said connexon component bacterium, and obtaining a heavy chain component plasmid comprising said HC from said heavy chain component bacterial library;
   4) obtaining a released LC from said light chain component plasmid, obtaining a released connexon from said connexon component plasmid, and obtaining a released HC from said heavy chain component plasmid;
   5) providing a display vector, and obtaining a released display vector fragment from said display vector;
   6) connecting the released LC, the released connexon, the released HC and the released display vector fragment to form a connection product for display;
   7) introducing said connection product for display into a fourth bacterium to obtain a display bacterial library of the antibody or the antibody fragment; and
   8) preparing said phage library displaying the antibody or the antibody fragment with said display bacterial library;
   wherein said first polynucleotide comprises a structure of R1-LC-R2 in the 5' to 3' direction, said second polynucleotide comprises a structure of R3-connexon-R4 in the 5' to 3' direction, said third polynucleotide comprises a structure of R5-HC-R6 in the 5' to 3' direction, and said display vector comprises a structure of R7-display vector fragment-R8 in the 5' to 3' direction, wherein the R1, R2, R3, R4, R5, R6, R7 and R8 are restriction endonuclease recognition sites, wherein, a terminal produced by cleaving said R2 with a restriction endonuclease can recognize and be connected to a terminal produced by cleaving said R3 with a restriction endonuclease, vice versa, and cannot recognize or be connected to a terminal produced by cleaving any one of said R1, R4, R5, R6, R7 and R8 with a restriction endonuclease, vice versa; a terminal produced by cleaving said R4 with a restriction endonuclease can recognize and be connected to a terminal produced by cleaving said R5 with a restriction endonuclease, vice versa; and cannot recognize or be connected to a terminal produced by cleaving any one of said R1, R2, R3, R6, R7 and R8 with a restriction endonuclease, vice versa; a terminal produced by cleaving said R6 with a restriction endonuclease can recognize and be connected to a terminal produced by cleaving said R7 with a restriction endonuclease, vice versa; and cannot recognize or be connected to a terminal produced by cleaving any one of said R1, R2, R3, R4, R5 and R8 with a restriction endonuclease, vice versa; and a terminal produced by cleaving said R8 with a restriction endonuclease can recognize and be connected to a terminal produced by cleaving said R1 with a restriction endonuclease, vice versa; and cannot recognize or be connected to a terminal produced by cleaving any one of said R2, R3, R4, R5, R6 and R7 with a restriction endonuclease, vice versa;
   wherein the 2) comprises digesting said first polynucleotide with a restriction endonuclease recognizing said R1 and R2, connecting the digested first polynucleotide to a light chain storage vector fragment to form a light chain storage connection product, and introducing said light chain storage connection product into said first bacterium to obtain said light chain component bacterial library; wherein said light chain storage vector comprises said R1 and R2, and said light chain storage vector fragment is obtained by digesting said light chain storage vector with a restriction endonuclease recognizing said R1 and R2;
   wherein the 2) comprises digesting said third polynucleotide with a restriction endonuclease recognizing said R5 and R6, connecting the digested third polynucleotide to a heavy chain storage vector fragment to form a heavy chain storage connection product, and introducing said heavy chain storage connection product into said third bacterium to obtain said heavy chain component bacterial library; wherein said heavy chain storage vector comprises said R5 and R6, and said heavy chain storage vector fragment is obtained by digesting said heavy chain storage vector with a restriction endonuclease recognizing said R5 and R6; and
   wherein the 2) comprises digesting said third polynucleotide with a restriction endonuclease recognizing said R5 and R6, connecting the digested third polynucleotide to a heavy chain storage vector fragment to form a heavy chain storage connection product, and introducing said heavy chain storage connection product into said third bacterium to obtain said heavy chain component bacterial library; wherein said heavy chain storage vector comprises said R5 and R6, and said heavy chain storage vector fragment is obtained by digesting said heavy chain storage vector with a restriction endonuclease recognizing said R5 and R6.
2. The method of claim 1, wherein said connection product for display in the 6) can express the light chain or the light chain fragment and the heavy chain or the heavy chain fragment in accordance with a reading frame under a condition suitable for expression of an antibody or an antibody fragment.

3. The method of claim 1, wherein said first polynucleotide, said second polynucleotide and said third polynucleotide are all linear nucleic acid molecules.

4. The method of claim 1, wherein said connexon comprises the nucleic acid sequence encoding a signal peptide pelB or a fragment thereof.

5. The method of claim 1, wherein a terminal produced by cleaving any one of said R1, R2, R3, R4, R5, R6, R7 and R8 with a restriction endonuclease is a non-palindrome sequence.

6. The method of claim 1, wherein two or more of said R1, R2, R3, R4, R5, R6, R7 and R8 can be recognized and cleaved with the same restriction endonuclease.

7. The method of claim 1, wherein said R1, R2, R3, R4, R5 and R8 can be recognized and cleaved with the same restriction endonuclease.

8. The method of claim 1, wherein said R6 and R7 can be recognized and cleaved with the same restriction endonuclease.

9. The method of claim 1, wherein said antibody or the fragment thereof comprises Fab, Fab', (Fab)2 and/or (Fab')2.

10. The method of claim 1, wherein said heavy chain storage vector comprises and comprises only a recognition site of BsmBI.

11. The method of claim 1, wherein the 2) comprises connecting said second polynucleotide to a vector fragment to form a connexon storage vector, and introducing said connexon storage vector into said second bacterium to obtain said connexon component bacterium.

12. The method of claim 11, wherein said connexon storage vector comprises said R3 and R4.

13. The method of claim 1, wherein the 4) comprises digesting said light chain component plasmid with a restriction endonuclease recognizing said R1 and R2, to obtain said released LC.

14. The method of claim 1, wherein the 4) comprises digesting said heavy chain component plasmid with a restriction endonuclease recognizing said R5 and R6, to obtain said released HC.

15. The method of claim 1, wherein the 4) comprises digesting said connexon storage vector with a restriction endonuclease recognizing said R3 and R4, to obtain said released connexon.

16. The method of claim 1, wherein the 4) comprises obtaining an amplification product from said connexon storage vector, said amplification product comprises said connexon, said R3 and said R4; and said amplification product is digested using a restriction endonuclease recognizing said R3 and R4, to obtain said released connexon.

17. The method of claim 1, wherein the 5) comprises digesting said display vector with a restriction endonuclease recognizing said R7 and R8 to release said display vector fragment.

18. The method of claim 1, wherein said display vector is derived from a pComb3x vector.

19. The method of claim 1, wherein three different digested fragments are obtained after said display vector is digested with a restriction endonuclease recognizing said R1, R2, R3, R4, R5 and R8.

20. The method of claim 1, wherein said display vector is linearized after said display vector is digested with a restriction endonuclease recognizing said R6 and R7.

21. The method of claim 1, wherein four different digested fragments are obtained after said display vector is digested with a restriction endonuclease recognizing said R1, R2, R3, R4, R5, R6, R7 and R8.

22. The method of claim 1, wherein the 2) comprises detecting samples from said light chain component bacterial library, said connexon component bacterium and/or said heavy chain component bacterial library to determine a library capacity and/or quality of said light chain component bacterial library, said connexon component bacterium and/or said heavy chain component bacterial library.

* * * * *